US006380373B1

(12) United States Patent
O'Malley et al.

(10) Patent No.: US 6,380,373 B1
(45) Date of Patent: *Apr. 30, 2002

(54) STEROID RECEPTOR COACTIVATOR COMPOSITIONS AND METHODS OF USE

(75) Inventors: Bert O'Malley; Ming-Jer Tsai; Sophia Y. Tsai; Sergio Onate, all of Houston, TX (US)

(73) Assignee: Baylor College of Medicine, Houston, TX (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/701,154

(22) Filed: Aug. 21, 1996

Related U.S. Application Data

(60) Provisional application No. 60/003,784, filed on Sep. 15, 1995.

(51) Int. Cl.$^7$ .............................................. C07H 21/04
(52) U.S. Cl. .................... 536/23.5; 536/23.1; 435/320.1
(58) Field of Search ............................. 536/23.1, 23.5, 536/24.3, 24.31; 435/320.1; 530/350; 514/44

(56) References Cited

U.S. PATENT DOCUMENTS

| | | | |
|---|---|---|---|
| 3,691,016 A | 9/1972 | Patel et al. | 195/68 |
| 3,969,287 A | 7/1976 | Jaworek et al. | 260/8 |
| 4,195,128 A | 3/1980 | Hildebrand et al. | 435/178 |
| 4,229,537 A | 10/1980 | Hodgins et al. | 435/177 |
| 4,247,642 A | 1/1981 | Hirohara et al. | 435/178 |
| 4,330,440 A | 5/1982 | Ayers et al. | 525/54.31 |
| 4,945,050 A | 7/1990 | Sanford et al. | 435/455 |
| 5,298,422 A | 3/1994 | Schwartz et al. | 435/320.1 |
| 5,364,791 A | 11/1994 | Vegeto et al. | 435/320.1 |

FOREIGN PATENT DOCUMENTS

| | | |
|---|---|---|
| WO | 9309236 | 5/1993 |
| WO | 9318759 | 9/1993 |
| WO | 9323431 | 11/1993 |

OTHER PUBLICATIONS

Cohen, J. Naked DNA points the way to vaccines. Science, vol. 259, pp. 1691–1692, Mar. 19, 1993.*
Orkin et al. Report and recommendations of the panel to assess the NIH investment in research on gene therapy. Distributed by the National Institutes of Health, Bethesda, MD., Dec. 17, 1995.*
Sequence Search of Seq. Id. No. 4, completed by the PTO's STIC in commercial databases on Sep. 23, 1997. Pp. 1 and 11–12 of a first set, and pp. 1–2 or a second set.*
Abe et al., "Molecular Characterization of a Novel Metabotropic Glutamate Receptor mGluR5 Coupled to Inositol Phosphate/Ca$^{2+}$ Signal Transduction," *J. Biol. Chem.* 267:13361–13368 (1992).

Adelman et al., "In Vitro Deletional Mutagenesis for Bacterial Production of the 20,000–Dalton Form of Human Pituitary Growth Hormone," *DNA* 2(3):183–193 (1983).
Allan et al., "Hormone and Antihormone Induce Distant Conformational Changes Which Are Central to Steroid Receptor Activation," *J. Biol. Chem.* 267:19513–19520 (1992).
Allan et al., "Ligand–dependent conformational changes in the progesterone receptor are necessary for events that follow DNA binding," *Proc. Natl. Acad. Sci. USA* 89:11750–11754 (1992).
Archer et al., "Transcriptional Factor Loading on the MMTV Promoter: A Bimodal Mechanism for Promoter Activation," *Science* 255:1573–1576 (1992).
Baniahmad et al., "A transferable silencing domain is present in the thyroid hormone receptor, in the v–erbA oncogene product and in the retinoic acid receptor," *EMBO J.* 11:1015–1023 (1992).
Baniahmad et al., "Enhancement of Human Estrogen Receptor Activity by SPT6: A Potential Coactivator," *Molecular Endocrinology* 9:34–43 (1995).
Baniahmad et al., "the τ4 Activation Domain of the Thyroid Hormone Receptor Is Required for Release of a Putative Corepressor(s) Necessary for Transcriptional Silencing," *Molecular and Cellular Biology* 15:76–86 (1995).
Baniahmad et al., "Interaction of human thyroid hormone receptor β with transcription factor TFIIB may mediate target gene derepression and activation by thyroid hormone," *Proc. Natl. Acad. Sci. USA* 90:8832–8836 (1993).
Bayer et al., "The Avidin–Biotin Complex in Affinity Cytochemistry," *Methods in Enzymology* 62:308–319 (1979).
Beekman et al., "A rapid one–step method to purify baculovirus–expressed human estrogen receptor to be used in the analysis of the oxytocin promoter," *Gene* 146:285–289 (1994).
Beekman et al., "Transcriptional Activation by the Estrogen Receptor Requires a Conformational Change in the Ligand Binding Domain," *Molecular Endocrinology* 7:1266–1274 (1993).
Benoist and Chambon, "In vivo sequence requirements of the SV40 early promoter region," *Nature* 290:304–310 (1981).
Berkenstam et al., "Cooperativity in Transactivation between Retinoic Acid Receptor and TFIID Requires an Activity Analogous to E1A," *Cell* 69:401–412 (1992).

(List continued on next page.)

Primary Examiner—Dave T. Nguyen
(74) Attorney, Agent, or Firm—Lyon & Lyon LLP

(57) ABSTRACT

The present invention relates to SRC-1 polypeptides, nucleic acids encoding such polypeptides, cells, tissues and animals containing such nucleic acids, antibodies to such polypeptides, assays utilizing such polypeptides, and methods relating to all of the foregoing. Methods for enhancing and inhibiting transcription by providing SRC-1 polypeptides or fragments thereof to a cell.

4 Claims, 5 Drawing Sheets

OTHER PUBLICATIONS

Bocquel et al., "The contribution of the N– and C–terminal regions of steroid receptors to activation of transcription is both receptor and cell–specific," *Nucleic Acids Research* 17:2581–2595 (1989).

Bollon and Stauver, "DNA Transformation Efficiency of Various Bacterial and Yeast Host–Vector Systems," *Journal of Clinical Hematology and Oncology* 10(2&3):39–48 (1980).

Botstein et al., "Making Mutations in vitro and Putting Them Back into Yeast," *Miami Winter Symposia* 19:265–274 (1982).

Brinster et al., "Factors affecting the efficiency of introducing foreign DNA into mice by microinjecting eggs," *Proc. Nat. Acad. Sci. USA* 82:4438–4442 (1985).

Broach, "The Yeast Plasmid 2μ Circle," *Cell* 28:203–204 (1982).

Broach, "The Yeast Plasmid 2μ Circle," in *The Molecular Biology of the Yeast Saccharomyces: Life Cycle and Inheritance*, Cold Spring Harbor Laboratory, Cold Spring Harbor, NY, pp. 445–470 (1981).

Bullock et al., "Techniques in Immunocytochemistry," Academic Press, Orlando, FL vol. 1(1982), vol. 2 (1983), vol. 3 (1985).

Campbell, "Monoclonal Antibody Technology: Laboratory Techniques in Biochemistry and Molecular Biology," Elsevier Science Publishers, Amsterdam, The Netherlands (1984) (Table of contents only).

Capecchi, "Altering the Genome by Homologous Recombination," *Science* 244:1288–1292 (1989).

Capecchi, "High Efficiency Transformation by Direct Microinjection of DNA into Cultured Mammalian Cells," *Cell* 22:479–488 (1980).

Cavailles et al., "Interaction of proteins with transcriptionally active estrogen receptors," *Proc. Natl. Acad. Sci. USA* 91:10009–10013 (1994).

Cavailles et al., "Nuclear factor RIP140 modulates transcriptional activation by the estrogen receptor," *EMBO Journal* 14(15):3741–3751 (1995).

Centiempo, "Prokaryotic gene expression in vitro: transcription–translation copuled systems," *Biochimie* 68:505–515 (1986).

Chalepakis et al., "Differential Gene Activation by Glucocorticoids and Progestins through the Hormone Regulatory Element of Mouse Mammary Tumor Virus," *Cell* 53:371–382 (1988).

Chard, "An Introduction to Radioimmunoassay and Related Techniques" Elsevier Science Publishers, Amsterdam, The Netherlands (1986) (Table of contents only).

Chater et al., "Streptomyces φC31–Like Phages: Cloning Vectors, Genome Changes and Host Range," in Sixth International Symposium on Actinomycetes, Akademiai Kaido, Budapest, Hungary, pp. 45–52 (1986).

Chen and Okayama, "High–Efficiency Transformation of Mammalian Cells by Plasmid DNA," *Molecular and Cellular Biology* 7(8):2745–2752 (1987).

Chiba et al., "Two human homologues of *Saccharomyces cerevisiae* SW12/SNF2 and *Drosophila brahma* are transcriptional coactivators cooperating with the estrogen receptor and the retinoic acid receptor," *Nucleic Acids Research* 22:1815–1820 (1994).

Chowdhury et al., "Long–term Improvement of Hypercholesterolemia After ex Vivo Gene Therapy in LDLF–Deficient Rabbits," *Science* 254:1802–1805 (1991).

Chrivia et al., "Phosphorylated CREB binds specifically to the nuclear protein CBP," *Nature* 365:855–859 (1993).

Chu et al., "Electroporation for the efficient transfection of mammalian cells with DNA," *Nucleic Acids Research* 15:1311–1326 (1987).

Chu et al., "Efficiency of Cytoplasmic Delivery by pH–Sensitive Liposomes to Cells in Culture," *Pharmaceutical Research* 7:824–834 (1990).

Conneely et al., "Promoter specific activating domains of the chicken progesterone receptor," in *Gene Regulation by Steroid Hormones IV*, edited by Roy and Clark, New York, Berlin, Heidelberg, London, Paris, Tokyo: Springer–Verlag, pp. 220–223 (1989).

Cooney et al., "Multiple Mechanisms of Chicken Ovalbumin Upstream Promoter Transcription Factor–dependent Repression of Transactivation by the Vitamin D, Thyroid Hormone, and Retinoic and Retinoic Acid Receptors," *J. Biol. Chem.* 268:4152–4160 (1993).

Courey and Tjian, "Analysis of Sp1 In Vivo Reveals Multiple Transcriptional Domains, Including a Novel Glutamine–Rich Activation Motif," *Cell* 55:887–898 (1988).

Creighton, *Proteins: Structures and Molecular Principles* pp. 79–86, W.H. Freeman and Co., New York (1983).

Cristiano et al., "Hepatic Gene Therapy: Adenovirus Enhancement of Receptor–Mediated Gene Delivery and Expression in Primary Hepatocytes," *Proc. Natl. Acad. Sci. USA* 90:2122–2126 (1993).

Curiel et al., "Adenovirus Enhancement of Transferrin–polylysine–mediated Gene Delivery," *Proc. Natl. Acad. Sci. USA* 88:8850–8854 (1991).

Curiel et al., "Gene Transfer to Respiratory Epithelial Cells via the Receptor–mediated Endocytosis Pathway," *Am. J. Respir. Cell. Mol. Biol.* 6:247–252 (1992).

DeMarzo et al., "Effects of the Steroid Antagonist RU486 on Dimerization of the Human Progesterone Receptor," *Biochemistry* 31:10491–10501 (1992).

Denner et al., "Regulation of Progesterone Receptor–Mediated Transcription by Phosphorylation," *Science* 250:1740–1743 (1990).

Durfee et al., "The retinoblastoma protein associates with the protein phosphatase type 1 catalytic subunit," *Genes and Development* 7:555–569 (1993).

Dynlacht et al., "Isolation of Coactivators Associated with the TATA–Binding Protein that Mediate Transcriptional Activation," *Cell* 66:563–576 (1991).

El–Ashry et al., "Human Progesterone Receptor Complexed with the Antagonist RU 486 Binds to Hormone Response Elements in a Structurally Altered Form," *Molecular Endocrinology* 3:1545–1558 (1989).

Engvall et al., "Enzyme–Linked Immunosorbent Assay, ELISA. III. Quantitation of Specific Antibodies by Enzyme–Labeled Anti–Immunoglobulin in Antigen–Coated Tubes," *J. Immunology* 109:129–135 (1972).

Felgner and Ringold, "Cationic liposome–mediated transfection," *Nature* 337:387–388 (1989).

Felgner et al., "Lipofection: A Highly Efficient, Lipid–mediated DNA–transfection Procedure," *Proc. Natl. Acad. Sci. USA* 84:7413–7417 (1987).

Flanagan et al., "A mediator required for activation of RNA polymerase II transcription in vitro," *Nature* 350:436–438 (1991).

Giguere et al., "Functional Domains of the Human Glucocorticoid Receptor," *Cell* 46:645–652 (1986).

Gilman et al., "Isolation of sigma–28–specific promoters from *Bacillus subtilis* DNA," *Gene* 32:11–32:11–20 (1984).

Glick and Whitney, "Factors affecting the expression of foreign proteins in *Escherichia coli*," *Journal of Industrial Microbiology* 1:277–282 (1987).

Goding, "Conjugation of Antibodies with Fluorochromes: Modifications to the Standard Methods," *J. Immunological Methods* 13:215–226 (1976).

Gold et al., "Translational Initiation in Prokaryotes," *Ann. Rev. Microbiol.* 35:365–403 (1981).

Gottesman, "Bacterial Regulation: Global Regulatory Networks," *Ann. Rev. Genet.* 18:415–441 (1984).

Gronemeyer, "Transcription Activation by Estrogen and Progesterone Receptors," *Ann. Rev. Genet.* 25:89–123 (1991).

Haensler and Szoka, "Haensler and Szoka, Synthesis and Characterization of a Trigalactosylated Bisacridine Compound to Target DNA to Hepatocytes," *Bioconjugate Chem.* 4:85–93 (1993).

Halachmi et al., "Estrogen Receptor–Associated Proteins: Possible Mediators of Hormone–Induced Transcription," *Science* 264:1455–1458 (1994).

Hamer and Walling, "Regulation In Vivo of a Cloned Mammalian Gene: Cadmium Induces the Transcription of a Mouse Metallothionein Gene in SV40 Vectors," *J. of Molecular and Applied Genetics* 1:273–288 (1982).

Hammer et al., "Spontaneous Inflammatory Disease in Transgenic Rats Expressing HLA–B27 and Human $\beta_2$m: An Animal Model of HLA–B27–Associated Human Disorders," *Cell* 63:1099–1112 (1990).

Haynes et al., "The bromodomain: a conserved sequence found in human, Drosophila and yeast proteins," *Nucleic Acids Research* 20:2603 (1992).

Helin et al., "Inhibition of E2F–1 Trasactivation by Direct Binding of the Retinoblastoma Protein," *Molecular and Cellular Biology* 13:6501–6508 (1993).

Hillier et al., "WashU–Merck EST Project," EMBL Database Entry HS15927, Accession No. T56159; Mar. 1, 1995.

Houdebine and Chourrout, "Transgenesis in Fish," *Experientia* 47:891–897 (1991).

Hurby et al., "Application of Synthetic Peptides: Antisense Peptides", in *Synthetic Peptides: A User's Guide,* edited by Gregory A. Grant, W.H. Freeman, NY, pp. 289–307 (1992).

Izaki, *Jpn. J. Bacteriol.* 33:729–742 (1978).

Wilchek and Jakoby, "The Literature on Affinity Chromatography," *Methods in Enzymology* 34:3–10 (1974).

Jasny, "Insect Viruses Invade Biotechnology," *Science* 238:1653 (1987).

John et al., "Plasmids as Epidemiologic Markers in Nosocomial Gram–Negative Bacilli: Experience at a University and Review of the Literature," *Rev. Infect. Dis.* 8:693–704 (1986).

Johnston and Hopper, "Isolation of the yeast regulatory gene GAS4 and analysis of its dosage effects on the galactose/melibiose regulon," *Proc. Natl. Acad. Sci. USA* 79:6971–6975 (1982).

Joyner et al., "Production of a mutation in mouse En–2 gene by homologous recombination in embryonic stem cells," *Nature* 338:153–156 (1989).

Kaneda et al., "The Improved Efficient Method for Introducing Macromolecules into Cells Using HVJ (Sendai Virus) Liposomes with Gangliosides," *Experimental Cell Research* 173:56–69 (1987).

Kaneda et al., "Increased Expression of DNA Cointroduced with Nuclear Protein in Adult Rat Liver," *Science* 243:375–378 (1989).

Kashanchi et al., "Direct interaction of human TFIID with the HIV–1 transactivator Tat," *Nature* 367:295–299 (1994).

Kasprzak et al., "Location of a Contact Site Between Actin and Myosin in the Three–Dimensional Structure of the Acto–S1 Complex," *Biochemistry* 28:9230–9238 (1989).

Kastner et al., "Two distinct estrogen–related promoters generate transcripts encoding the two functionally different human progesterone receptor forms A and B," *EMBO J.* 9:1603–1614 (1990).

Kendall and Cohen, "Plasmid Transfer in *Streptomyces lividans:* Identification of a kil–kor System Associated with the Transfer Region of PIJ101," *Journal of Bacteriology* 169:4177–4183 (1987).

Klein–Hitpass et al., "The Progesterone Receptor Stimulates Cell–Free Transcription by Enhancing the Formation of a Stable Perinitiation Complex," *Cell* 60:247–257 (1990).

Laurent et al., "The yeast SNF2/SW12 protein has DNA–stimulated ATPase activity required for transcriptional activation," *Genes and Development* 7:583–591 (1993).

Lengendre and Szoka, "Cyclic Amphiphatic Peptide–DNA Complexes Mediate High–efficiency Transfection of Adherent Mammalian Cells," *Proc. Natl. Acad. Sci. USA* 90:893–897 (1993).

Legendre and Szoka, "Delivery of Plasmid DNA into Mammalian Cell Lines Using pH–Sensitive Liposomes: Comparison with Cationic Liposomes," *Pharmaceutical Research* 9:1235–1242 (1992).

Le Douarin et al., "The N–terminal part of TIF1, a putative mediator of the ligand–dependent activation function (AF–2) of nuclear receptors, is fused to B–raf in the oncogenic protien T18," *EMBO J.* 14:2020–2023 (1995).

Lutz et al., "The Distribution of Two hnRNP–Associated Protein Defined by a Monoclonal Antibody is Altered in Heat–Shocked HeLa Cells," *Exp. Cell Res.* 175:109–124 (1988).

Maniatis, "Ch. 11—Recombinant DNA Procedures in the Study of Eukaryotic Genes," in *Cell Biology: A Comprehensive Treatise,* vol. 3, Gene Sequence Expression, Academic Press, NY, pp. 563–608 (1980).

McDonnell et al., "Identification of a negative regulatory function for steroid receptors," *Proc. Natl. Acad. Sci. USA* 89:10563–10567 (1992).

McKnight, "Functional Relationships between Transcriptional Control Signals of the Thymidine Kinase Gene of Herpes Simplex Virus," *Cell* 31:355–365 (1982).

Meyer et al., "Agonistic and antagonistic activities of RU486 on the functions of the human progesterone receptor," *EMBO J.* 9:3923–3932 (1990).

Meyer et al., "Steroid Hormone Receptors Compete for Factors That Mediate Their Enhancer Function," *Cell* 57:433–442 (1989).

Miller, "Human gene therapy comes of age," *Nature* 357:455–460 (1992).

Miller et al., "An Insect Baculovirus Host–Vector System for High–Level Expression of Foreign Genes," in *Genetic Engineering: Principles and Methods,* edited by Setlow et al., Plenum Press, 8:277–298 (1986).

Muchardt and Yaniv, "A human homologue of *Saccharomyces cerevisiae* SNF2/SW12 and *Drosophila brm* genes potentiates transcriptional activation by the glucocorticoid receptor," *EMBO J.* 12:4279–4290 (1993).

Mulligan, "The Basic Science of Gene Therapy," *Science* 260:926–932 (1993).

Nawaz et al., "The yeast SIN3 gene product negatively regulates the activity of the human progesterone receptor and positively regulates the activities of GAL4 and the HAP1 activator," *Mol. Gen. Genet.* 245:724–733 (1994).

Nelson et al., "Detection of Acridinium Esters by Chemiluminescence," in *Nonisotopic DNA Probe Techniques,* Kricka editor, Academic Press, Inc., San Diego, pp. 275–310 (1992).

Okayama and Berg, "A cDNA Cloning Vector That Permits Expression of cDNA Inserts in Mammalian Cells," *Molecular and Cellular Biology* 3:280–289 (1983).

Onate et al., "Sequence and characterization of a coactivator for the steorid hormone receptor superfamily," *Science* 270:1354–1357 (1995).

Pereira et al., "The 56 kDa Androgen Protein is an Aldehyde Dehydrogenase," *Biochemical and Biophysical Research Communications* 175:831–838 (1991).

Pursel et al., "Genetic Engineering of Livestock," *Science* 244:1281–1288 (1989).

Raineri et al., "Analysis of human immunodefiency virus type 1 promoter insertion in vivo," EMBL Database Entry HS19179, Accession No. U19179; Apr. 13, 1995.

Sartorius et al., "A Third Transaction Function (AF3) of Human Progesterone Receptors Located in the Unique N–Terminal Segment of the B–isoform," *Molecular Endocrinology* 8:1347–1360 (1994).

Sauer et al., "Control of transcription by Kruppel through interactions with TFIIB and TFIIEβ," *Nature* 375:162–164 (1995).

Schild et al., "A nucleosome–dependent static loop potentiates estrogen–regulated transcription from the Xenopus vitellogenin B1 promoter in vitro," *EMBO J.* 12:423–433 (1993).

Seol et al., "Isolation of Proteins That Interact Specifically with the Retinoid X Receptor: Two Novel Orphan Receptors," *Molecular Endocrinology* 9:72–85 (1995).

Shemshedini et al., "In Vitro Activity of the Transcription Activation Functions of the Progesterone Receptor," *J. Biol. Chem.* 267:1834–1839 (1992).

Silver et al., "Amino terminus of the yeast GAL4 gene product is sufficient for nuclear localization," *Proc. Natl. Acad. Sci. USA* 81:5951–5955 (1984).

Simons et al., "Gene Transfer Into Sheep," *Bio/Technology* 6:179–183 (1988).

Singh et al., "A role for retinoblastoma protein in potentiating transcriptional activation by the glucocorticoid receptor," *Nature* 374:562–565 (1995).

Smith et al., "Modulation of the ligand–dependent activation of the human estrogen receptor by hormone and antihormone," *Proc. Natl. Acad. Sci. USA* 90:6120–6124 (1993).

St. Groth and Scheidegger, "Production of Monoclonal Antibodies: Strategy and Tactics," *J. Immunol. Methods* 35:1–21 (1980).

Sternberger et al., "The Unlabeled Antibody Enzyme Method of Immunohistochemistry," *Histochemistry and Cytochemistry* 18:315–333 (1970).

Stringer et al., "Direct and selective binding of an acidic transcriptional activation domain to the TAT–box factor TFIID," *Nature* 345:783–785 (1990).

Tasset et al., "Distinct Classes of Transcriptional Activating Domains Function by Different Mechanisms," *Cell* 62:1177–1187 (1990).

Tijssen, "Practice and Theory of Enzyme Immunoassays: Laboratory Techniques in Biochemistry and Molecular Biology", Elsevier Science Publishers, Amsterdam, The Netherlands (1985) (Table of contents only).

Tora et al., "The N–terminal region of the chicken progesterone receptor specifies target gene activation," *Nature* 333:185–188 (1988).

Tora et al., "The Human Estrogen Receptor has Two Independent Nonacidic Transcriptional Activation Functions," *Cell* 59:477–487 (1989).

Truss et al., "Hormone induces binding of receptors and transcription factors to a rearranged nucleosome on the MMTV promoter in vivo," *EMBO J.* 14:1737–1751 (1995).

Tsai et al., "Recombinant Human Glucocorticoid Receptor Induces Transcription of Hormone Response Genes in Vitro," *J. Biol. Chem.* 265:17055–17061 (1990).

Tsai and O'Malley, "Molecular Mechanisms of Action of Steroid/Thyroid Receptor Superfamily Members," *Ann. Rev. Biochem.* 63:451–486 (1994).

Tung et al., "Antagonist–Occupied Human Progesterone B–Receptors Activate Transcription without Binding to Progesterone Response Elements and Are Dominantly inhibited by A–Receptors," *Molecular Endocrinology* 7:1256–1265 (1993).

Ulmanen et al., "Transcription and Translation of Foreign Genes in *Bacillus subtilis* by the Aid of a Secretion Vector," *Journal of Bacteriology* 162:176–182(1985).

Umesono et al., "Direct Repeats as Selective Response Elements for the Thyroid Hormone, Retinoic Acid, and Vitamin $D_3$ Receptors," *Cell* 65:1255–12661 (1991).

Vegeto et al., "The Mechanism of RU486 Antagonism Is Dependent on the Conformation of the Carboxy–Terminal Tail of the Human Progesterone Receptor," *Cell* 69:703–713 (1992).

Voegel et al., "TIF2, a 160 kDa transcriptional mediator for the ligand–dependent activation function AF–2 of nuclear receptors," *EMBO J.* 15:3667–3675 (1996).

Ward et al., "Construction and characterization of a series of multi–copy promoter–probe plasmid vectors for Streptomyces using the aminoglycoside phosphotransferase gene from Tn5 as indicator," *Mol. Gen. Genet.* 203:468–478 (1986).

Wei et al., "Immunologic Analysis of Human Breast Cancer Progesterone Receptors. 2. Structure, Phosphorylationn, and Processing," *Biochemistry* 26:6262–6272 (1987).

Weigel et al., "Ligands Induce Conformational Changes in the Carboxyl–Terminus of Progesterone Receptors which are Detected by a Site–Directed Antipeptide Monoclonal Antibody," *Molecular Endocrinology* 6:1585–1597 (1992).

Dreborg et al., "Ch. 10—The chemistry and standardization of allergens," in *Handbook of Experimental Immunology— Volume 1: Immunochemistry,* 4th Ed., edited by Weir et al., Blackwell Scientific Publications, Oxford, England, pp. 10.1–10.28 (1986).

Wilson et al., "Clinical Protocol: Ex Vivo Gene Therapy of Familial Hypercholesterolemia," *Human Gene Therapy* 3:179–222 (1991).

Wolff et al., "Direct Gene Transfer into Mouse Muscle In Vivo," *Science* 247:1465–1468 (1990).

Wu and Wu, "Receptor–mediated in Vitro Gene Transformation by a Soluble DNA Carrier System," *J. Biol. Chem.* 262:4429–4432 (1987).

Wu et al., "Receptor–mediated Gene Delivery in Vivo," *J. Biol. Chem.* 266:14338–14342 (1991).

Yang et al., "In Vivo and In Vitro Gene Transfer to Mammalian Somatic Cells by Particle Bombardment," *Proc. Natl. Acad. Sci. USA* 87:9568–9572 (1990).

Yoshinaga et al., "Roles of SWI1, SW12, and SW13 Proteins for Transcriptional Enhancement by Steroid Receptors," *Science* 258:1598–1604 (1992).

Zawel and Reinberg, "Common Themes in Assembly and Function of Eukaryotic Transcription Complexes," *Ann. Rev. Biochem.* 64:533–561 (1995).

Zhu et al., "Systemic Gene Expression After Intravenous DNA Delivery into Adult Mice," *Science* 261:209–211 (1993).

* cited by examiner

```
-56  ATATCATCGACAGGGAGCACAGTGGGCTTTCTCCTCAAGATGACACTAATTCTGGA          -1

1  ATG TCA ATT CCC CGA GTA AAT CCC TCG GTC AAT CCT AGT ATC TCT    45
 (1)  M   S   I   P   R   V   N   P   S   V   N   P   S   I   S   (15)

46  CCA GCT CAT GGT GTG GCT CGT TCA TCC ACA TTG CCA CCA TCC AAC    90
(17)  P   A   H   G   V   A   R   S   S   T   L   P   P   S   N   (30)

97  AGC AAC ATG GTA TCC ACC AGA ATA AAC CGC CAG CAG AGC TCA GAC   135
(33)  S   N   M   V   S   T   R   I   N   R   Q   Q   S   S   D   (45)

145  CTT CAT AGC AGC AGT CAT AGT AAT TCT AGC AAC AGC CAA GGA AGT   180
(46)  L   H   S   S   S   H   S   N   S   S   N   S   Q   G   S   (60)

181  TTC GGA TGC TCA CCC GGA AGT CAG ATT GTA GCC AAT GTT GCC TTA   225
(61)  F   G   C   S   P   G   S   Q   I   V   A   N   V   A   L   (75)

226  AAC AAA GGA CAG GCC AGT TCA CAG AGC AGT AAA CCC TCT TTA AAC   270
(76)  N   K   G   Q   A   S   S   Q   S   S   K   P   S   L   N   (90)

271  CTC AAT AAT CCT CCT ATG GAA GGT ACA GGA ATA TCC CTA GCA CAG   315
(91)  L   N   N   P   P   M   E   G   T   G   I   S   L   A   Q  (105)

316  TTC ATG TCT CCA AGG AGA CAG GTT ACT TCT GGA TTG GCA ACA AGG   360
(106) F   M   S   P   R   R   Q   V   T   S   G   L   A   T   R  (120)

361  CCC AGG ATG CCA AAC AAT TCC TTT CCT CCT AAT ATT TCG ACA TTA   405
(121) P   R   M   P   N   N   S   F   P   P   N   I   S   T   L  (135)

406  AGC TCT CCC GTT GGC ATG ACA AGT AGT GCC TGT AAT AAT AAT AAC   450
(136) S   S   P   V   G   M   T   S   S   A   C   N   N   N   N  (150)

451  CGA TCT TAT TCA AAC ATC CCA GTA ACA TCT TTA CAG GGT ATG AAT   495
(151) R   S   Y   S   N   I   P   V   T   S   L   Q   G   M   N  (165)

496  GAA GGA CCC AAT AAC TCC GTT GGC TTC TCT GCC AGT TCT CCA GTC   540
(166) E   G   P   N   N   S   V   G   F   S   A   S   S   P   V  (180)

541  CTC AGG CAG ATG AGC TCA CAG AAT TCA CCT AGC AGA TTA AAT ATA   585
(181) L   R   Q   M   S   S   Q   N   S   P   S   R   L   N   I  (195)

586  CAA CCA GCA AAA GCT GAG TCC AAA GAT AAC AAA GAG ATT GCC TCA   630
(196) Q   P   A   K   A   E   S   K   D   N   K   E   I   A   S  (210)

631  ACT TTA AAT GAA ATG ATT CAA TCT GAC AAC AGC TCT AGT GAT GGC   675
(209) T   L   N   E   M   I   Q   S   D   N   S   S   S   D   G  (225)
```

FIG. 1A

```
 676 AAA CCT CTG GAT TCA GGG CTT CTG CAT AAC AAT GAC AGA CTT TCA  720
(226) K   P   L   D   S   G   L   L   H   N   N   D   R   L   S  (240)

721 GAT GGA GAC AGT AAA TAC TCT CAA ACC AGT CAC AAA CTA GTG CAG  765
(241) D   G   D   S   K   Y   S   Q   T   S   H   K   L   V   Q  (255)

766 CTT TTG ACA ACA ACT GCC GAA CAG CAG TTA CGG CAT GCT GAT ATA  810
(256) L   L   T   T   T   A   E   Q   Q   L   R   H   A   D   I  (270)

811 GAC ACA AGC TGC AAA GAT GTC CTG TCT TGC ACA GGC ACT TCC AAC  855
(271) D   T   S   C   K   D   V   L   S   C   T   G   T   S   N  (285)

856 TCT GCC TCT GCT AAC TCT TCA GGA GGT TCT TGT CCC TCT TCT CAT  900
(286) S   A   S   A   N   S   S   G   G   S   C   P   S   S   H  (300)

901 AGC TCA TTG ACA GCA CGG CAT AAA ATT CTA CAC CGG CTC TTA CAG  945
(305) A   R   H   K   I   L   H   R   L   L   Q   E   G   S   P  (315)

946 GAG GGT AGC CCC TCA GAT ATC ACC ACT TTG TCT GTC GAG CCT GAT  990
(316) S   S   S   L   T   D   I   T   T   L   S   V   E   P   D  (330)

991 AAA AAG GAC AGT GCA TCT ACT TCT GTG TCA GTG ACT GGA CAG GTA 1035
(331) K   K   D   S   A   S   T   S   V   S   V   T   G   Q   V  (345)

1036 CAA GGA AAC TCC AGT ATA AAA CTA GAA CTG GAT GCT TCA AAG AAA 1080
(346) Q   G   N   S   S   I   K   L   E   L   D   A   S   K   K  (360)

1081 AAA GAA TCA AAA GAC CAT CAG CTC CTA CGC TAT CTT TTA GAT AAA 1125
(361) K   E   S   K   D   H   Q   L   L   R   Y   L   L   D   K  (375)

1126 GAT GAG AAA GAT TTA AGA TCA ACT CCA AAC CTG AGC CTG GAT GAT 1170
(376) D   E   K   D   L   R   S   T   P   N   L   S   L   D   D  (390)

1171 GTA AAG GTG AAA GTG GAA AAG AAA GAA CAG ATG GAT CCA TGT AAT 1215
(391) V   K   V   K   V   E   K   K   E   Q   M   D   P   C   N  (405)

1216 ACA AAC CCA ACC CCA ATG ACG AAG GCC ACT CCT GAG GAA ATA AAA 1260
(406) T   N   P   T   P   M   T   K   A   T   P   E   E   I   K  (420)

1261 CTG GAG GCC CAG AGC CAG TTT ACA GCT GAC CTT GAC CAG TTT GAT 1305
(421) L   E   A   Q   S   Q   F   T   A   D   L   D   Q   F   D  (435)

1306 CAG TTA CTG CCC ACG CTG GAG AAG GCA GCA CAG TTG CCA GGC TTA 1350
(436) Q   L   L   P   T   L   E   K   A   A   Q   L   P   G   L  (450)

1351 TGT GAG ACA GAC AGG ATG GAT GGT GCG GTC ACC AGT GTA ACC ATC 1395
(451) C   E   T   D   R   M   D   G   A   V   T   S   V   T   I  (465)
```

FIG. 1B

```
1396  AAA TCG GAG ATC CTG CCA GCT TCA CTT CAG TCC GCC ACT GCC AGA  1440
(466)  K   S   E   I   L   P   A   S   L   Q   S   A   T   A   R   (480)

1441  CCC ACT TCC AGG CTG AAT AGA TTA CCT GAG CTG GAA TTG GAA GCA  1485
(481)  P   T   S   R   L   N   R   L   P   E   L   E   L   E   A   (495)

1486  ATT GAT AAC CAA TTT GGA CAA CCA GGA ACA GGC GAT CAG ATT CCA  1530
(496)  I   D   N   Q   F   G   Q   P   G   T   G   D   Q   I   P   (510)

1531  TGG ACA AAT AAT ACA GTG ACA GCT ATA AAT CAG AGT AAA TCA GAA  1575
(511)  W   T   N   N   T   V   T   A   I   N   Q   S   K   S   E   (525)

1576  GAC CAG TGT ATT AGC TCA CAA TTA GAT GAG CTT CTC TGT CCA CCC  1620
(526)  D   Q   C   I   S   S   Q   L   D   E   L   L   C   P   P   (540)

1621  ACA ACA GTA GAA GGG AGA AAT GAT GAG AAG GCT CTT CTT GAA CAG  1665
(541)  T   T   V   E   G   R   N   D   E   K   A   L   L   E   Q   (555)

1666  CTG GTA TCC TTC CTT AGT GGC AAA GAT GAA ACT GAG CTA GCT GAA  1710
(556)  L   V   S   F   L   S   G   K   D   E   T   E   L   A   E   (570)

1711  CTA GAC AGA GCT CTG GGA ATT GAC AAA CTT GTT CAG GGG GGT GGA  1755
(571)  L   D   R   A   L   G   I   D   K   L   V   Q   G   G   G   (585)

1756  TTA GAT GTA TTA TCA GAG AGA TTT CCA CCA CAA CAA GCA ACG CCA  1800
(586)  L   D   V   L   S   E   R   F   P   P   Q   Q   A   T   P   (600)

1801  CCT TTG ATC ATG GAA GAA AGA CCC AAC CTT TAT TCC CAG CCT TAC  1845
(601)  P   L   I   M   E   E   R   P   N   L   Y   S   Q   P   Y   (615)

1846  TCT TCT CCT TTT CCT ACT GCC AAT CTC CCT AGC CCT TTC CAA GGC  1890
(616)  S   S   P   F   P   T   A   N   L   P   S   P   F   Q   G   (630)

1891  ATG GTC AGG CAA AAA CCT TCA CTG GGG ACG ATG CCT GTT CAA GTA  1935
(631)  M   V   R   Q   K   P   S   L   G   T   M   P   V   Q   V   (645)

1936  ACA CCT CCC CGA GGT GCT TTT TCA CCT GGC ATG GGC ATG CAG CCC  1980
(646)  T   P   P   R   G   A   F   S   P   G   M   G   M   Q   P   (660)

1981  AGG CAA ACT CTA AAC AGA CCT CCG GCT GCA CCT AAC CAG CTT CGA  2025
(661)  R   Q   T   L   N   R   P   P   A   A   P   N   Q   L   R   (675)

2026  CTT CAA CTA CAG CAG CGA TTA CAG GGA CAA CAG CAG TTG ATA CAC  2070
(676)  L   Q   L   Q   Q   R   L   Q   G   Q   Q   Q   L   I   H   (690)

2071  CAA AAT CGG CAA GCT ATC TTA AAC CAG TTT GCA GCA ACT GCT CCT  2115
(691)  Q   N   R   Q   A   I   L   N   Q   F   A   A   T   A   P   (705)
```

FIG. 1C

```
2116  GTT GGC ATC AAT ATG AGA TCA GGC ATG CAA CAG CAA ATT ACA CCT  2160
(706)  V   G   I   N   M   R   S   G   M   Q   Q   Q   I   T   P  (720)

2161  CAG CCA CCC CTG AAT GCT CAA ATG TTG GCA CAA CGT CAG CGG GAA  2205
(721)  Q   P   P   L   N   A   Q   M   L   A   Q   R   Q   R   E  (735)

2206  CTG TAC AGT CAA CAG CAC CGA CAG AGG CAG CTA ATA CAG CAG CAA  2250
(736)  L   Y   S   Q   Q   H   R   Q   R   Q   L   I   Q   Q   Q  (750)

2251  AGA GCC ATG CTT ATG AGG CAG CAA AGC TTT GGG AAC AAC CTC CCT  2295
(751)  R   A   M   L   M   R   Q   Q   S   F   G   N   N   L   P  (765)

2296  CCC TCA TCT GGA CTA CCA GTT CAA ACG GGG AAC CCC CGT CTT CCT  2340
(769)  P   S   S   G   L   P   V   Q   T   G   N   P   R   L   P  (780)

2341  CAG GGT GCT CCA CAG CAA TTC CCC TAT CCA CCA AAC TAT GGT ACA  2385
(781)  Q   G   A   P   Q   Q   F   P   Y   P   P   N   Y   G   T  (795)

2386  AAT CCA GGA ACC CCA CCT GCT TCT ACC AGC CCG TTT TCA CAA CTA  2430
(796)  N   P   G   T   P   P   A   S   T   S   P   F   S   Q   L  (810)

2431  GCA GCA AAT CCT GAA GCA TCC TTG GCC AAC CGC AAC AGC ATG GTG  2475
(811)  A   A   N   P   E   A   S   L   A   N   R   N   S   M   V  (825)

2476  AGC AGA GGC ATG ACA GGA AAC ATA GGA GGA CAG TTT GGC ACT GGA  2520
(826)  S   R   G   M   T   G   N   I   G   G   Q   F   G   T   G  (840)

2521  ATC AAT CCT CAG ATG CAG CAG AAT GTC TTC CAG TAT CCA GGA GCA  2565
(841)  I   N   P   Q   M   Q   Q   N   V   F   Q   Y   P   G   A  (855)

2566  GGA ATG GTT CCC CAA GGT GAG GCC AAC TTT GCT CCA TCT CTA AGC  2610
(856)  G   M   V   P   Q   G   E   A   N   F   A   P   S   L   S  (870)

2611  CCT GGG AGC TCC ATG GTG CCG ATG CCA ATC CCT CCT CCT CAG AGT  2655
(871)  P   G   S   S   M   V   P   M   P   I   P   P   P   Q   S  (885)

2656  TCT CTG CTC CAG CAA ACT CCA CCT GCC TCC GGG TAT CAG TCA CCA  2700
(886)  S   L   L   Q   Q   T   P   P   A   S   G   Y   Q   S   P  (900)

2701  GAC ATG AAG GCC TGG CAG CAA GGA GCG ATA GGA AAC AAC AAT GTG  2745
(913)  D   M   K   A   W   Q   Q   G   A   I   G   N   N   N   V  (915)

2746  TTC AGT CAA GCT GTC CAG AAC CAG CCC ACG CCT GCA CAG CCA GGA  2790
(916)  F   S   Q   A   V   Q   N   Q   P   T   P   A   Q   P   G  (930)

2791  GTA TAC AAC AAC ATG AGC ATC ACC GTT TCC ATG GCA GGT GGA AAT  2835
(931)  V   Y   N   N   M   S   I   T   V   S   M   A   G   G   N  (945)
```

FIG. 1D

```
2836  ACG AAT GTT CAG AAC ATG AAC CCA ATG ATG GCC CAG ATG CAG ATG  2880
(946)  T   N   V   Q   N   M   N   P   M   M   A   Q   M   Q   M  (960)

2881  AGC TCT TTG CAG ATG CCA GGA ATG AAC ACT GTG TGC CCT GAG CAG  2925
(961)  S   S   L   Q   M   P   G   M   N   T   V   C   P   E   Q  (975)

2926  ATA AAT GAT CCC GCA CTG AGA CAC ACA GGC CTC TAC TGC AAC CAG  2970
(976)  I   N   D   P   A   L   R   H   T   G   L   Y   C   N   Q  (990)

2977  CTC TCA TCC ACT GAC CTT CTC AAA ACA GAA GCA GAT GGA ACC CAG  3015
(993)  L   S   S   T   D   L   L   K   T   E   A   D   G   T   Q  (1005)

3016  CAG GTG CAA CAG GTT CAG GTG TTT GCT GAC GTC CAG TGT ACA GTG  3060
(1006) Q   V   Q   Q   V   Q   V   F   A   D   V   Q   C   T   V  (1020)

3061  AAT CTG GTA GGC GGG GAC CCT TAC CTG AAC CAG CCT GGT CCA CTG  3105
(1021) N   L   V   G   G   D   P   Y   L   N   Q   P   G   P   L  (1035)

3106  GGA ACT CAA AAG CCC ACG TCA GGA CCA CAG ACC CCC CAG GCC CAG  3150
(1036) G   T   Q   K   P   T   S   G   P   Q   T   P   Q   A   Q  (1050)

3161  CAG AAG AGC CTC CTT CAG CAG CTA CTG ACT GAA TAA CCACTTTTAAA  3197
(1051) Q   K   S   L   L   Q   Q   L   L   T   E   *               (1061)

3208  GGA ATG TGA AATTTAAATAATAGACATACAGAGATATACAAATATATTATATATTT  3253

3254  TTCTGAGATTTTTGATATCTCAATCTGCAGCCATTCTTCAGGTCGTAGCATTTGGAGCA  3312

3313  AAAAAAAAAAAAAAAAATCG                                          3332
```

FIG. 1E

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 19 base pairs
      (B) TYPE: nucleic acid

```
            (C) STRANDEDNESS:        single
            (D) TOPOLOGY:            linear (xi) SEQUENCE DESCRIPTION: SEQ ID NO: 1:

CGCCATGGTC CTTGGAGGT                                                      19

(2) INFORMATION FOR SEQ ID NO: 2:

(i) SEQUENCE CHARACTERISTICS:
            (A) LENGTH:              33 base pairs
            (B) TYPE:                nucleic acid
            (C) STRANDEDNESS:        single
            (D) TOPOLOGY:            linear (xi) SEQUENCE DESCRIPTION: SEQ ID NO: 2:

AAGTCGACAC ATTCACTTTT TATGAAAGAG AAG                                      33

(2) INFORMATION FOR SEQ ID NO: 3:

(i) SEQUENCE CHARACTERISTICS:
            (A) LENGTH:              24 base pairs
            (B) TYPE:                nucleic acid
            (C) STRANDEDNESS:        single
            (D) TOPOLOGY:            linear (xi) SEQUENCE DESCRIPTION: SEQ ID NO: 3:

GGAATTCCCG ACGTTGTGCC AACA                                                24

(2) INFORMATION FOR SEQ ID NO: 4:

(i) SEQUENCE CHARACTERISTICS:
            (A) LENGTH:              3388 base pairs
            (B) TYPE:                nucleic acid
            (C) STRANDEDNESS:        single
            (D) TOPOLOGY:            linear (xi) SEQUENCE DESCRIPTION: SEQ ID NO: 4:

ATATCATCGA CAGGGAGCAC AGTGGGCTTT CTCCTCAAGA TGACACTAAT TCTGGAATGT         60

CAATTCCCCG AGTAAATCCC TCGGTCAATC CTAGTATCTC TCCAGCTCAT GGTGTGGCTC         120

GTTCATCCAC ATTGCCACCA TCCAACAGCA ACATGGTATC CACCAGAATA AACCGCCAGC         180

AGAGCTCAGA CCTTCATAGC AGCAGTCATA GTAATTCTAG CAACAGCCAA GGAAGTTTCG         240

GATGCTCACC CGGAAGTCAG ATTGTAGCCA ATGTTGCCTT AAACAAAGGA CAGGCCAGTT         300

CACAGAGCAG TAAACCCTCT TTAAACCTCA ATAATCCTCC TATGGAAGGT ACAGGAATAT         360

CCCTAGCACA GTTCATGTCT CCAAGGAGAC AGGTTACTTC TGGATTGGCA CAAGGCCCA         420

GGATGCCAAA CAATTCCTTT CCTCCTAATA TTTCGACATT AAGCTCTCCC GTTGGCATGA         480

CAAGTAGTGC CTGTAATAAT AATAACCGAT CTTATTCAAA CATCCCAGTA ACATCTTTAC         540

AGGGTATGAA TGAAGGACCC AATAACTCCG TTGGCTTCTC TGCCAGTTCT CCAGTCCTCA         600

GGCAGATGAG CTCACAGAAT TCACCTAGCA GATTAAATAT ACAACCAGCA AAAGCTGAGT         660

CCAAAGATAA CAAAGAGATT GCCTCAACTT TAAATGAAAT GATTCAATCT GACAACAGCT         720

CTAGTGATGG CAAACCTCTG GATTCAGGGC TTCTGCATAA CAATGACAGA CTTTCAGATG         780

GAGACAGTAA ATACTCTCAA ACCAGTCACA AACTAGTGCA GCTTTTGACA CAACTGCCG          840

AACAGCAGTT ACGGCATGCT GATATAGACA CAAGCTGCAA AGATGTCCTG TCTTGCACAG         900

GCACTTCCAA CTCTGCCTCT GCTAACTCTT CAGGAGGTTC TTGTCCCTCT TCTCATAGCT         960

CATTGACAGC ACGGCATAAA ATTCTACACC GGCTCTTACA GGAGGGTAGC CCCTCAGATA         1020

TCACCACTTT GTCTGTCGAG CCTGATAAAA AGGACAGTGC ATCTACTTCT GTGTCAGTGA         1080
```

-continued

```
CTGGACAGGT ACAAGGAAAC TCCAGTATAA AACTAGAACT GGATGCTTCA AGAAAAAAG    1140

AATCAAAAGA CCATCAGCTC CTACGCTATC TTTTAGATAA AGATGAGAAA GATTTAAGAT    1200

CAACTCCAAA CCTGAGCCTG GATGATGTAA AGGTGAAAGT GGAAAAGAAA GAACAGATGG    1260

ATCCATGTAA TACAAACCCA ACCCCAATGA CGAAGGCCAC TCCTGAGGAA ATAAAACTGG    1320

AGGCCCAGAG CCAGTTTACA GCTGACCTTG ACCAGTTTGA TCAGTTACTG CCCACGCTGG    1380

AGAAGGCAGC ACAGTTGCCA GGCTTATGTG AGACAGACAG GATGGATGGT GCGGTCACCA    1440

GTGTAACCAT CAAATCGGAG ATCCTGCCAG CTTCACTTCA GTCCGCCACT GCCAGACCCA    1500

CTTCCAGGCT GAATAGATTA CCTGAGCTGG AATTGGAAGC AATTGATAAC CAATTTGGAC    1560

AACCAGGAAC AGGCGATCAG ATTCCATGGA CAAATAATAC AGTGACAGCT ATAAATCAGA    1620

GTAAATCAGA AGACCAGTGT ATTAGCTCAC AATTAGATGA GCTTCTCTGT CCACCCACAA    1680

CAGTAGAAGG GAGAAATGAT GAGAAGGCTC TTCTTGAACA GCTGGTATCC TTCCTTAGTG    1740

GCAAAGATGA AACTGAGCTA GCTGAACTAG ACAGAGCTCT GGGAATTGAC AAACTTGTTC    1800

AGGGGGGTGG ATTAGATGTA TTATCAGAGA GATTTCCACC ACAACAAGCA ACGCCACCTT    1860

TGATCATGGA AGAAAGACCC AACCTTTATT CCCAGCCTTA CTCTTCTCCT TTTCCTACTG    1920

CCAATCTCCC TAGCCCTTTC CAAGGCATGG TCAGGCAAAA ACCTTCACTG GGGACGATGC    1980

CTGTTCAAGT AACACCTCCC CGAGGTGCTT TTTCACCTGG CATGGGCATG CAGCCCAGGC    2040

AAACTCTAAA CAGACCTCCG GCTGCACCTA ACCAGCTTCG ACTTCAACTA CAGCAGCGAT    2100

TACAGGGACA ACAGCAGTTG ATACACCAAA ATCGGCAAGC TATCTTAAAC CAGTTTGCAG    2160

CAACTGCTCC TGTTGGCATC AATATGAGAT CAGGCATGCA ACAGCAAATT ACACCTCAGC    2220

CACCCCTGAA TGCTCAAATG TTGGCACAAC GTCAGCGGGA ACTGTACAGT CAACAGCACC    2280

GACAGAGGCA GCTAATACAG CAGCAAAGAG CCATGCTTAT GAGGCAGCAA AGCTTTGGGA    2340

ACAACCTCCC TCCCTCATCT GGACTACCAG TTCAAACGGG GAACCCCGT CTTCCTCAGG     2400

GTGCTCCACA GCAATTCCCC TATCCACCAA ACTATGGTAC AAATCCAGGA ACCCCACCTG    2460

CTTCTACCAG CCCGTTTTCA CAACTAGCAG CAAATCCTGA AGCATCCTTG GCCAACCGCA    2520

ACAGCATGGT GAGCAGAGGC ATGACAGGAA ACATAGGAGG ACAGTTTGGC ACTGGAATCA    2580

ATCCTCAGAT GCAGCAGAAT GTCTTCCAGT ATCCAGGAGC AGGAATGGTT CCCCAAGGTG    2640

AGGCCAACTT TGCTCCATCT CTAAGCCCTG GGAGCTCCAT GGTGCCGATG CCAATCCCTC    2700

CTCCTCAGAG TTCTCTGCTC CAGCAAACTC CACCTGCCTC CGGGTATCAG TCACCAGACA    2760

TGAAGGCCTG GCAGCAAGGA GCGATAGGAA ACAACAATGT GTTCAGTCAA GCTGTCCAGA    2820

ACCAGCCCAC GCCTGCACAG CCAGGAGTAT ACAACAACAT GAGCATCACC GTTTCCATGG    2880

CAGGTGGAAA TACGAATGTT CAGAACATGA ACCCAATGAT GGCCCAGATG CAGATGAGCT    2940

CTTTGCAGAT GCCAGGAATG AACACTGTGT GCCCTGAGCA GATAAATGAT CCCGCACTGA    3000

GACACACAGG CCTCTACTGC AACCAGCTCT CATCCACTGA CCTTCTCAAA ACAGAAGCAG    3060

ATGGAACCCA GCAGGTGCAA CAGGTTCAGG TGTTTGCTGA CGTCCAGTGT ACAGTGAATC    3120

TGGTAGGCGG GGACCCTTAC CTGAACCAGC CTGGTCCACT GGGAACTCAA AAGCCCACGT    3180

CAGGACCACA GACCCCCCAG GCCCAGCAGA GAGCCTCCT TCAGCAGCTA CTGACTGAAT     3240

AACCACTTTT AAAGGAATGT GAAATTTAAA TAATAGACAT ACAGAGATAT ACAAATATAT    3300

TATATATTTT TCTGAGATTT TTGATATCTC AATCTGCAGC CATTCTTCAG GTCGTAGCAT    3360

TTGGAGCAAA AAAAAAAAAA AAAAATCG                                      3388
```

(2) INFORMATION FOR SEQ ID NO: 5:

(i) SEQUENCE CHARACTERISTICS:
        (A) LENGTH: 1061 amino acids
        (B) TYPE: amino acid
        (C) STRANDEDNESS: single
        (D) TOPOLOGY: linear (xi) SEQUENCE DESCRIPTION: SEQ ID NO: 5:

```
Met Ser Ile Pro Arg Val Asn Pro Ser Val Asn Pro Ser Ile Ser Pro
  1               5                  10                  15

Ala His Gly Val Ala Arg Ser Ser Thr Leu Pro Pro Ser Asn Ser Asn
                 20                  25                  30

Met Val Ser Thr Arg Ile Asn Arg Gln Gln Ser Ser Asp Leu His Ser
         35                  40                  45

Ser Ser His Ser Asn Ser Ser Asn Ser Gln Gly Ser Phe Gly Cys Ser
     50                  55                  60

Pro Gly Ser Gln Ile Val Ala Asn Val Ala Leu Asn Lys Gly Gln Ala
 65                  70                  75                  80

Ser Ser Gln Ser Ser Lys Pro Ser Leu Asn Leu Asn Asn Pro Pro Met
                 85                  90                  95

Glu Gly Thr Gly Ile Ser Leu Ala Gln Phe Met Ser Pro Arg Arg Gln
                100                 105                 110

Val Thr Ser Gly Leu Ala Thr Arg Pro Arg Met Pro Asn Asn Ser Phe
            115                 120                 125

Pro Pro Asn Ile Ser Thr Leu Ser Ser Pro Val Gly Met Thr Ser Ser
130                 135                 140

Ala Cys Asn Asn Asn Arg Ser Tyr Ser Asn Ile Pro Val Thr Ser
145                 150                 155                 160

Leu Gln Gly Met Asn Glu Gly Pro Asn Asn Ser Val Gly Phe Ser Ala
                165                 170                 175

Ser Ser Pro Val Leu Arg Gln Met Ser Ser Gln Asn Ser Pro Ser Arg
            180                 185                 190

Leu Asn Ile Gln Pro Ala Lys Ala Glu Ser Lys Asp Asn Lys Glu Ile
            195                 200                 205

Ala Ser Thr Leu Asn Glu Met Ile Gln Ser Asp Asn Ser Ser Ser Asp
210                 215                 220

Gly Lys Pro Leu Asp Ser Gly Leu Leu His Asn Asn Asp Arg Leu Ser
225                 230                 235                 240

Asp Gly Asp Ser Lys Tyr Ser Gln Thr Ser His Lys Leu Val Gln Leu
                245                 250                 255

Leu Thr Thr Thr Ala Glu Gln Gln Leu Arg His Ala Asp Ile Asp Thr
            260                 265                 270

Ser Cys Lys Asp Val Leu Ser Cys Thr Gly Thr Ser Asn Ser Ala Ser
            275                 280                 285

Ala Asn Ser Ser Gly Gly Ser Cys Pro Ser Ser His Ser Ser Leu Thr
290                 295                 300

Ala Arg His Lys Ile Leu His Arg Leu Leu Gln Glu Gly Ser Pro Ser
305                 310                 315                 320

Asp Ile Thr Thr Leu Ser Val Glu Pro Asp Lys Lys Asp Ser Ala Ser
                325                 330                 335

Thr Ser Val Ser Val Thr Gly Gln Val Gln Gly Asn Ser Ser Ile Lys
            340                 345                 350

Leu Glu Leu Asp Ala Ser Lys Lys Glu Ser Lys Asp His Gln Leu
            355                 360                 365
```

-continued

Leu Arg Tyr Leu Leu Asp Lys Asp Glu Lys Asp Leu Arg Ser Thr Pro
    370                 375                 380

Asn Leu Ser Leu Asp Asp Val Lys Val Lys Val Glu Lys Lys Glu Gln
385                 390                 395                 400

Met Asp Pro Cys Asn Thr Asn Pro Thr Pro Met Thr Lys Ala Thr Pro
            405                 410                 415

Glu Glu Ile Lys Leu Glu Ala Gln Ser Gln Phe Thr Ala Asp Leu Asp
                420                 425                 430

Gln Phe Asp Gln Leu Leu Pro Thr Leu Glu Lys Ala Ala Gln Leu Pro
            435                 440                 445

Gly Leu Cys Glu Thr Asp Arg Met Asp Gly Ala Val Thr Ser Val Thr
        450                 455                 460

Ile Lys Ser Glu Ile Leu Pro Ala Ser Leu Gln Ser Ala Thr Ala Arg
465                 470                 475                 480

Pro Thr Ser Arg Leu Asn Arg Leu Pro Glu Leu Glu Leu Glu Ala Ile
                485                 490                 495

Asp Asn Gln Phe Gly Gln Pro Gly Thr Gly Asp Gln Ile Pro Trp Thr
            500                 505                 510

Asn Asn Thr Val Thr Ala Ile Asn Gln Ser Lys Ser Glu Asp Gln Cys
        515                 520                 525

Ile Ser Ser Gln Leu Asp Glu Leu Leu Cys Pro Pro Thr Thr Val Glu
        530                 535                 540

Gly Arg Asn Asp Glu Lys Ala Leu Leu Glu Gln Leu Val Ser Phe Leu
545                 550                 555                 560

Ser Gly Lys Asp Glu Thr Glu Leu Ala Glu Leu Asp Arg Ala Leu Gly
                565                 570                 575

Ile Asp Lys Leu Val Gln Gly Gly Gly Leu Asp Val Leu Ser Glu Arg
            580                 585                 590

Phe Pro Pro Gln Gln Ala Thr Pro Pro Leu Ile Met Glu Glu Arg Pro
        595                 600                 605

Asn Leu Tyr Ser Gln Pro Tyr Ser Ser Pro Phe Pro Thr Ala Asn Leu
        610                 615                 620

Pro Ser Pro Phe Gln Gly Met Val Arg Gln Lys Pro Ser Leu Gly Thr
625                 630                 635                 640

Met Pro Val Gln Val Thr Pro Pro Arg Gly Ala Phe Ser Pro Gly Met
                645                 650                 655

Gly Met Gln Pro Arg Gln Thr Leu Asn Arg Pro Pro Ala Ala Pro Asn
            660                 665                 670

Gln Leu Arg Leu Gln Leu Gln Gln Arg Leu Gln Gly Gln Gln Gln Leu
        675                 680                 685

Ile His Gln Asn Arg Gln Ala Ile Leu Asn Gln Phe Ala Ala Thr Ala
        690                 695                 700

Pro Val Gly Ile Asn Met Arg Ser Gly Met Gln Gln Ile Thr Pro
705                 710                 715                 720

Gln Pro Pro Leu Asn Ala Gln Met Leu Ala Gln Arg Gln Arg Glu Leu
            725                 730                 735

Tyr Ser Gln Gln His Arg Gln Arg Gln Leu Ile Gln Gln Arg Ala
            740                 745                 750

Met Leu Met Arg Gln Gln Ser Phe Gly Asn Asn Leu Pro Pro Ser Ser
        755                 760                 765

Gly Leu Pro Val Gln Thr Gly Asn Pro Arg Leu Pro Gln Gly Ala Pro
770                 775                 780

```
Gln Gln Phe Pro Tyr Pro Pro Asn Tyr Gly Thr Asn Pro Gly Thr Pro
785                 790                 795                 800

Pro Ala Ser Thr Ser Pro Phe Ser Gln Leu Ala Ala Asn Pro Glu Ala
                805                 810                 815

Ser Leu Ala Asn Arg Asn Ser Met Val Ser Arg Gly Met Thr Gly Asn
            820                 825                 830

Ile Gly Gly Gln Phe Gly Thr Gly Ile Asn Pro Gln Met Gln Gln Asn
        835                 840                 845

Val Phe Gln Tyr Pro Gly Ala Gly Met Val Pro Gln Gly Glu Ala Asn
    850                 855                 860

Phe Ala Pro Ser Leu Ser Pro Gly Ser Ser Met Val Pro Met Pro Ile
865                 870                 875                 880

Pro Pro Pro Gln Ser Ser Leu Leu Gln Gln Thr Pro Pro Ala Ser Gly
                885                 890                 895

Tyr Gln Ser Pro Asp Met Lys Ala Trp Gln Gln Gly Ala Ile Gly Asn
                900                 905                 910

Asn Asn Val Phe Ser Gln Ala Val Gln Asn Gln Pro Thr Pro Ala Gln
            915                 920                 925

Pro Gly Val Tyr Asn Asn Met Ser Ile Thr Val Ser Met Ala Gly Gly
    930                 935                 940

Asn Thr Asn Val Gln Asn Met Asn Pro Met Met Ala Gln Met Gln Met
945                 950                 955                 960

Ser Ser Leu Gln Met Pro Gly Met Asn Thr Val Cys Pro Glu Gln Ile
            965                 970                 975

Asn Asp Pro Ala Leu Arg His Thr Gly Leu Tyr Cys Asn Gln Leu Ser
            980                 985                 990

Ser Thr Asp Leu Leu Lys Thr Glu Ala Asp Gly Thr Gln Gln Val Gln
        995                 1000                1005

Gln Val Gln Val Phe Ala Asp Val Gln Cys Thr Val Asn Leu Val Gly
    1010                1015                1020

Gly Asp Pro Tyr Leu Asn Gln Pro Gly Pro Leu Gly Thr Gln Lys Pro
1025                1030                1035                1040

Thr Ser Gly Pro Gln Thr Pro Gln Ala Gln Gln Lys Ser Leu Leu Gln
                1045                1050                1055

Gln Leu Leu Thr Glu
                1060
```

STEROID RECEPTOR COACTIVATOR COMPOSITIONS AND METHODS OF USE

RELATED APPLICATIONS

This application is related to provisional application Ser. No. 60/003,784, filed Sep. 15, 1995, which is incorporated herein by reference in its entirety, including any drawings and figures.

The invention described herein was developed in part with funds provided by the Untied States Public Health Service of the Department of Health and Human Services, Grant Number HD-08188. The Government has certain rights.

FIELD OF THE INVENTION

The present invention relates to the novel protein termed steroid receptor coactivator-one ("SRC-1"), nucleotide sequences encoding SRC-1, as well as various products and methods useful for augmenting or downregulating the activity of one or more steroid receptors.

BACKGROUND OF THE INVENTION

The following description of the background of the invention is provided to aid in understanding the invention but is not admitted to be prior art to the invention.

Transcription is a fundamental biological process whereby an RNA molecule is formed upon a DNA template by complementary base pairing that is mediated by RNA polymerase II. Accumulated evidence indicates that numerous general transcription factors undergo a defined order of assembly at promoter-DNA elements to assure RNA polymerase II binding and initiation of transcription of target genes (for review see Zawel, L. and Reinberg, D. (1995), *Ann. Rev. Biochem.* 64, 533–561).

Activation of transcription can be achieved by direct interaction of activators with one or more components of the basal transcriptional machinery. Direct interaction between activators and the basal transcription machinery has been described for several activators (Stringer, K. F. et al., (1990), *Nature* 345, 783–785; Kashanchi, F. et al., (1994), *Nature* 367, 295–299; Sauer, F. et al., (1995), *Nature* 375, 162–164).

Optimal transactivation by an activator is likely to require additional factors termed adaptors or coactivators. These factors seem to play a key regulatory role in bridging or stabilizing the activator with general transcription factors in the core transcriptional machinery. The ability of an activator to squelch or inhibit transactivation of a target gene by another transactivator suggests that they compete for a limited amount of cofactor(s) required for the transactivation process and furthers the concept that coactivators are required for efficient transactivational function (Flanagan, P. M. et al., (1991), *Nature* 350, 436–438).

It has been postulated that steroid receptors regulate transcription via interactions with the basal transcriptional machinery. However, the finding that squelching occurs between members of the steroid receptor superfamily, indicates that an additional factor(s) or coactivator(s) is important for efficient ligand-inducible target gene expression by members of this superfamily (Meyer, M. E. et al., (1989), *Cell* 57, 433–442; Conneely, O. M. et al., (1989), "Promoter specific activating domains of the chicken progesterone receptor." In Gene Regulation by Steroid Hormones IV. A. K. Roy and J. Clark, eds. (New York, Berlin, Heidelberg, London, Paris, Tokyo: Springer-Verlag), pp. 220–223; Bocquel, M. T. et al., (1989), *Nucleic Acids Res.* 17, 2581–2594; Shemshedini, L. et al., (1992), *J. Biol. Chem.* 261, 1834–1839). No such functional coactivator for this superfamily has previously been identified.

Steroid receptors belong to a superfamily of ligand inducible transcription factors which regulate hormone responsive genes and thereby affect several biological processes including cell growth and differentiation. The steroid/thyroid hormone receptor superfamily can be divided into two types (termed A and B) based on their characteristic association with heat shock proteins, binding to DNA and their ligand-dependent transactivation function (Tsai, M. -J. and O'Malley, B. W. (1994), *Ann. Rev. Biochem.* 63, 451–486).

One steroid receptor, the human progesterone receptor (hPR), is expressed in cells as two isoforms: $PR_B$ of 120 kDa and $PR_A$ of 94 kDa. The A isoform is a shorter transcript of PR, lacking the most N-terminal 164 amino acids of the B receptor (Kastner, P. et al., (1990), *EMBO J.* 9, 1603–1614; Wei, L. L et al., (1987), *Biochem.* 26, 6262–6272). Although they display similar ligand specificities and DNA-binding affinities in vitro, the transcriptional activity of the two receptor isoforms show different promoter and cell specificities when assayed in intact cells (Chalepakis, G. et al., (1988), *Cell* 53, 371–382; Tora, L. et al., (1988), *Nature* 333, 185–188; Tung, L. et al., (1993), *Mol. Endocrinol.* 7, 1256–1265).

Like other members of the steroid receptor superfamily, the hPRs are modular proteins containing a ligand binding domain (LBD) at the C-terminus and a centrally located DNA binding domain (DBD). Two regions in hPR have been thought to contain transcriptional activation functions (AFs). One is located at the N-terminus (AF1) and the other (AF2) is located within the LBD (Tora, L. et al., (1989), *Cell* 59, 477–487; Gronemeyer, H. (1991), *Ann. Rev. Genet.* 25, 89–123). Recent results indicate that the $hPR_B$specific 164 amino acid fragment may contain an additional activation function (Sartorius, C. A. et al., (1994), *Mol. Endocrinol.* 8, 1347–1360) that is required for maximal transactivation of the full-length receptor.

Activation of a steroid receptor is a complex multi-step process that involves structural and functional alterations of receptor which promote specific binding to DNA hormone-responsive elements (HREs) to modulate the target gene expression (for review see Tsai, M. -J. and O'Malley, B. W. (1994), *Ann. Rev. Biochem.* 63, 451–486). Thus, steroid receptors must undergo a rather complex multi-step activation process to achieve their ultimate transactivational function.

Coactivators have been implicated widely in nuclear steroid receptor function. Transcriptional interference experiments between members of the steroid receptor superfamily suggested that coactivators are limiting and interact, either directly or indirectly, with the receptor protein in vivo to modulate transcription. However, as noted above, no such functional coactivator for this superfamily has previously been identified.

SUMMARY OF THE INVENTION

The present invention relates to SRC-1 polypeptides, nucleic acids encoding such polypeptides, cells containing such nucleic acids, antibodies to such gene products, assays utilizing such polypeptides, and methods relating to all of the foregoing. In particular, this invention relates to methods for augmenting or downregulating the activity of one or more steroid receptors.

The present invention is based upon the isolation and characterization of a new protein which we have designated steroid receptor coactivator-1, or SRC-1. We have determined that modulation of SRC-1 activity is useful in therapeutic procedures and thus the present invention provides several agents and methods useful for modulating steroid hormone responses and activities, including modulation of the activity of other transactivators.

The isolated, purified, and/or enriched SRC-1 polypeptides and/or nucleic acids can be used to transactivate a steroid receptor and thereby promote the level of transcription in an organisms or cell. Administration of the appropriate material can be accomplished by one skilled in the art using methods described herein. For example, one or more transfected and/or transformed cells can be used to perform a gene therapy based treatment where activity of steroid receptors may be involved. Examples of disorders or conditions that involve the activity of steroid receptors include malignancies of the reproductive endocrine system and inflamation and immunity disorders, such as those described in U.S. patent application Ser. No. 08/479,913, filed Jun. 7, 1995, incorporated herein by reference in its entirety, including any drawings. Examples of other disorders or conditions are listed in references available to those skilled in the art such as the Physicians' Desk Reference and include endocrine disorders, rheumatic disorders, collagen disorders, dermatologic diseases, allergic states, ophthalmic diseases, gastrointestinal diseases, respitory diseases, hematologic disorders, breast cancer, endometriosis, hyperproliferative disorders including cancer and others. Alternatively, methods of the invention may be used to inhibit transcription. For example, a truncated form of SRC-1 can be used as a dominant negative inhibitor of receptor activity.

We describe herein the cloning and characterization of a cDNA encoding a protein required for hPR transactivational function, hereafter termed steroid receptor coactivator-one (SRC-1). SRC-1 directly and specifically interacts with the ligand binding domain (LBD) of hPR in a hormone-dependent manner. Binding of the antagonist RU486 to the receptor protein abolishes this interaction. Coexpression of SRC-1 with steroid receptors enhances (>10 fold) the hormone-induced transcription of a cellular target gene without altering the basal activity. Furthermore, overexpression of SRC-1 can reverse the ability of ER to squelch PR-mediated transactivation. Finally, coexpression of a truncated form of SRC-1, which retains the ability to interact with receptor, results in a dominant-negative inhibition of receptor activity. SRC-1 thus encodes a protein that fulfills the properties of a coactivator which ensures efficient ligand-dependent activity of steroid receptors on target genes.

Thus, in a first aspect the invention features an isolated, enriched, or purified nucleic acid encoding a SRC-1 polypeptide.

By "a SRC-1 polypeptide" is meant 25 (preferably 30, more preferably 35, most preferably 40) or more contiguous amino acids set forth in the full length amino acid sequence of FIGS. 1A–1E, or a functional derivative thereof as described herein. In certain aspects, polypeptides of 50, 100, 425, 430, 435, 440 or more amino acids are preferred. The SRC-1 polypeptide can be encoded by a full-length nucleic acid sequence or any portion of the full-length nucleic acid sequence, so long as a functional activity of the polypeptide is retained. Such functional activity can be, for example, (1) the ability to interact with the PR in an agonist specific manner, (2) the ability to enhance the hormone-induced transcriptional activity without altering basal activity of the promoter, (3) the ability to stimulate transactiviation of one or all steroid receptors, (4) the ability to reverse ER squelching of hPR activation in a dose dependent manner; and/or (5) the ability of a truncated form of the SRC-1 polypeptide to inhibit receptor activity in a dominant negative manner. The amino acid sequence is preferably substantially similar to the sequence shown in FIGS. 1A–1E, or fragments thereof. A sequence that is substantially similar will have at least 90% identity (preferably at least 95% and most preferably 99–100%) to the sequence of FIGS. 1A–1E.

By "identity" is meant a property of sequences that measures their similarity or relationship. Identity is measured by dividing the number of identical residues by the total number of residues and multiplying the product by 100. Thus, two copies of exactly the same sequence have 100% identity, but sequences that are less highly conserved and have deletions, additions, or replacements may have a lower degree of identity. Those skilled in the art will recognize that several computer programs are available for determining sequence identity.

By "isolated" in reference to nucleic acid is meant a polymer of 2 (preferably 21, more preferably 39, most preferably 75) or more nucleotides conjugated to each other, including DNA or RNA that is isolated from a natural source or that is synthesized. In certain embodiments of the invention longer nucleic acids are preferred, for example those of 1202, 1221, 1239, 1275 or more nucleotides and/or those having at least 50%, 60%, 75%, 90%, 95% or 99% identity to the full length sequence shown in FIGS. 1A–1E. The isolated nucleic acid of the present invention is unique in the sense that it is not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only nucleotide chain present, but that it is essentially free (about 90–95% pure at least) of non-nucleotide material naturally associated with it and thus is meant to distinguish from isolated chromosomes.

By the use of the term "enriched" in reference to nucleic acid is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased. The term significant here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level this level should be at least 2–5 fold greater, e.g., in terms of mg/ml). Individual clones isolated from a cDNA library may be purified to electrophoretic homogeneity. The claimed DNA molecules obtained from these clones could be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated.

In preferred embodiments the isolated nucleic acid comprises, consists essentially of, or consists of a nucleic acid sequence set forth in the full length amino acid sequence of FIGS. 1A–1E, a functional derivative thereof, or encodes at least 75, 90, 105, 120, 150, 475, 490, 505, 520, or 550 contiguous amino acids thereof; the SRC-1 polypeptide comprises, consists essentially of, or consists of at least 25, 30, 35, or 40 contiguous amino acids of a SRC-1 polypeptide. The nucleic acid may be isolated from a natural source by cDNA cloning or subtractive hybridization; the natural source may be mammalian (human) blood, semen, or tissue and the nucleic acid may be synthesized by the triester method or by using an automated DNA synthesizer. In yet other preferred embodiments the nucleic acid is a conserved or unique region, for example those useful for the design of hybridization probes to facilitate identification and cloning of additional polypeptides, the design of PCR probes to facilitate cloning of additional polypeptides, and obtaining antibodies to polypeptide regions.

By "conserved nucleic acid regions", are meant regions present on two or more nucleic acids encoding a SRC-1 polypeptide, to which a particular nucleic acid sequence can hybridize under lower stringency conditions. Examples of lower stringency conditions suitable for screening for nucleic acid encoding SRC-1 polypeptides are provided in Abe, et al. *J. Biol. Chem.*, 19:13361 (1992) (hereby incorporated by reference herein in its entirety, including any drawings). Preferably, conserved regions differ by no more than 5 out of 20 nucleotides.

By "unique nucleic acid region" is meant a sequence present in a full length nucleic acid coding for a SRC-1 polypeptide that is not present in a sequence coding for any other naturally occurring polypeptide. Such regions preferably comprise 30 or 45 contiguous nucleotides present in the full length nucleic acid encoding a SRC-1 polypeptide. In particular, a unique nucleic acid region is preferably of mammalian origin.

The invention also features a nucleic acid probe for the detection of a SRC-1 polypeptide or nucleic acid encoding a SRC-1 polypeptide in a sample. The nucleic acid probe contains nucleic acid that will hybridize to a sequence set forth in FIGS. 1A–1E or a functional derivative thereof. The SRC-1 polypeptide that is detected may comprise, consist of, or consist essentially of any given number of contiguous amino acids of the amino acid sequence set forth in FIGS. 1A–1E.

By "comprising" it is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

In preferred embodiments the nucleic acid probe hybridizes to nucleic acid encoding at least 12, 25, 50, 75, 90, 100, 120, 150, 412, 425, 450, 475, 490, 500, 520, or 550 contiguous amino acids of the full-length sequence set forth in FIGS. 1A–1E or a functional derivative thereof. Various low or high stringency hybridization conditions may be used depending upon the specificity and selectivity desired. Under stringent hybridization conditions only highly complementary, nucleic acid sequences hybridize. Preferably, such conditions prevent hybridization of nucleic acids having 1 or 2 mismatches out of 20 contiguous nucleotides.

Methods for using the probes include detecting the presence or amount SRC-1 RNA in a sample by contacting the sample with a nucleic acid probe under conditions such that hybridization occurs and detecting the presence or amount of the probe bound to SRC-1 RNA. The nucleic acid duplex formed between the probe and a nucleic acid sequence coding for a SRC-1 polypeptide may be used in the identification of the sequence of the nucleic acid detected (for example see, Nelson et al., in *Nonisotopic DNA Probe Techniques*, p. 275 Academic Press, San Diego (Kricka, ed., 1992) hereby incorporated by reference herein in its entirety, including any drawings). Kits for performing such methods may be constructed to include a container means having disposed therein a nucleic acid probe.

The invention also features recombinant nucleic acid, preferably in a cell or an organism. The invention also provides a recombinant cell or tissue containing a purified nucleic acid coding for a SRC-1 polypeptide. The recombinant nucleic acid may contain a sequence set forth in FIGS. 1A–1E or a functional derivative thereof and a vector or a promoter effective to initiate transcription in a host cell. The recombinant nucleic acid can alternatively contain a transcriptional initiation region functional in a cell, a sequence complimentary to an RNA sequence encoding a SRC-1 polypeptide and a transcriptional termination region functional in a cell. In such cells, the nucleic acid may be under the control of its genomic regulatory elements, or may be under the control of exogenous regulatory elements including an exogenous promoter. By "exogenous" it is meant a promoter that is not normally coupled in vivo transcriptionally to the coding sequence for the SRC-1 polypeptide.

In other aspects, the invention provides transgenic, non-human mammals containing a transgene encoding a SRC-1 polypeptide or a gene effecting the expression of a SRC-1 polypeptide. Such transgenic nonhuman mammals are particularly useful as an in vivo test system for studying the effects of introducing a SRC-1 polypeptide, regulating the expression of a SRC-1 polypeptide (i.e., through the introduction of additional genes, antisense nucleic acids, or ribozymes).

A "transgenic animal" is an animal having cells that contain DNA which has been artificially inserted into a cell, which DNA becomes part of the genome of the animal which develops from that cell.

Preferred transgenic animals are primates, mice, rats, cows, pigs, horses, goats, sheep, dogs and cats. The transgenic DNA may encode for a human SRC-1 polypeptide. Native expression in an animal may be reduced by providing an amount of anti-sense RNA or DNA effective to reduce expression of the receptor.

In other embodiments a steroid ligand activates a molecular switch (as described herein and in is U.S. patent application Ser. No. 07/939,246, filed Sep. 2, 1992 and 08/479,913, filed Jun. 7, 1995 both of which are incorporated herein by reference in their entirety including any drawings) and the SRC-1 polypeptide and thereby provides a superphysiological response to enhance steroid therapy. Expression of the SRC-1 polypeptide may be driven by a constitutively active promoter with a coding region for SRC-1. The gene switch may optionally be provided either in the same plasmid or in a different plasmid. The promoter for SRC-1 may be regulated by a gene switch so that the ligand activates both SRC-1 and the gene of interest.

In another aspect the present invention provides a method for increasing the transcription of a target gene. Transcription refers to the process of converting genetic information from DNA to RNA. The method involves the step of providing nucleic acid encoding a SRC-1 polypeptide to a cell containing said target gene. The increase may be from an initial level of no transcription or may be from a pre-existing level of transcription. The target gene can be any gene that is transactivated by SRC-1. The level of transcription may be determined using methods known in the art; for example the level of transcription may be assessed by measuring the chloramphenicol acetyl transferase activity. Providing SRC-1 nucleic acid, or the polypeptide itself, to a cell can increase the transcriptional activity of any steroid receptor, such as the mineral corticoid (MR), androgen (AR), estrogen, progesterone, Vitamin D, COUP-TF, cis-retonic acid, Nurr-1, thyroid hormone, mineralocorticoid, glucocorticoid-α, glucocorticoid-β and orphan receptors.

In preferred embodiments the method may also involve the step of providing a molecular switch for regulating expression of a nucleic acid cassette in gene therapy to the cell containing the target gene. The molecular switch includes a natural steroid receptor DNA binding domain linked to a modified ligand binding domain. Preferably the SRC-1 polypeptide comprises the full length amino acid sequence of FIGS. 1A–1E (SEQ ID NO:5)or a fragment thereof having at least 700, 800, or 900 contiguous amino acids of the full length sequence, or a fragment containing an essential interaction domain of SRC-1. The switch is preferably tissue specific, as described herein.

The method may also involve: (1) attaching the molecular switch to a nucleic acid cassette to form a nucleic acid cassette/molecular switch complex for use in the gene therapy; (2) administering a pharmacological dose of the nucleic acid cassette/molecular switch complex to an animal or human to be treated; (3) turning the molecular switch on or off by dosing the animal or human with a pharmacological dose of a ligand which binds to the modified ligand binding site; and (4) transcribing the nucleic acid to produce a protein after the animal or human is given a pharmacological dose of the ligand. These steps are described and definitions for terms such as "nucleic acid cassette", and "plasmid" are provided in U.S. patent application Ser. No. 07/939,246, filed Sep. 2, 1992 and International Patent Publication WO 93/23431, published Nov. 25, 1993, both of which are incorporated herein by reference in their entirety including any drawings.

The molecular switch and the nucleic acid cassette may be on the same or separate plasmids and may be co-injected into a target cell or injected separately. Similarly, the molecular switch and the nucleic acid encoding the SRC-1 polypeptide may be on the same or separate plasmids and may be co-injected or separately injected into a target cell.

In another aspect the invention provides a composition of matter comprising a molecular switch linked to a nucleic acid cassette. The cassette/molecular switch complex is positionally and sequentially oriented in a vector such that the nucleic acid in the cassette can be transcribed and when necessary translated in a target cell. The molecular switch regulates a constitutively active promoter in a plasmid with a coding region for a SRC-1 polypeptide.

The invention also features a method for decreasing the transcription of a target gene. The method involves providing nucleic acid encoding a dominant-negative inhibitor of a SRC-1 polypeptide in a cell containing said target gene. The dominant negative inhibitor preferably is encoded by a N truncated fragment of the full length sequence, such as the approximately 150 amino acid long fragment of Example 8.

In another aspect the present invention provides a molecular switch for regulating expression of a nucleic acid cassette in gene therapy, comprising a modified SRC-1 polypeptide, said polypeptide including a natural SRC-1 activation domain linked to a modified binding domain. In this embodiment the SRC-1 nucleic acid forms part of the molecular switch. Thus, a substitution is envisioned in a previosly described switch which included a DNA binding domain of a steroid receptor (for example GAL-4) linked to a transactivation domain (for example VP-16) linked to ligand binding domain (for example a mutated LBD of the progesterone receptor). The substitution involves replacing VP-16 or some other transactivation domain with an essential interaction domain of SRC-1. The term "essential interaction domain" refers to the portion of SRC-1 required for interaction with other transcriptional factors and agents and those skilled in the art may locate an essential interaction domain using techniques known in the art.

The invention also features a method for regulating expression of a nucleic acid cassette in gene therapy comprising the step of attaching a modified SRC-1 polypeptide molecular switch to a nucleic acid cassette to form a nucleic acid/molecular switch complex for use in gene therapy and administering a pharmacological dose of the nucleic acid cassette/molecular switch complex to an animal or human to be treated.

In another aspect the invention features a composition of matter comprising a modified SRC-1 polypeptide molecular switch linked to a nucleic acid cassette, wherein said complex is positionally oriented in a vector such that the nucleic acid in the cassette can be transcribed and when necessary translated in a target cell.

The invention also features a method of treating a SRC-1 related disease or condition (such as those described herein which require modulation of steroid receptor activity) comprising the steps of inserting an expression vector containing a SRC-1 coding sequence into cells, growing the cells in vitro, and infusing the cells into a patient in need of such treatment.

The summary of the invention described above is non-limiting and other features and advantages of the invention will be apparent from the following description of the preferred embodiments, and from the claims.

BRIEF DESCRIPTION OF THE DRAWINGS

FIGS. 1A–1E shows the nucleotide and amino acid sequences of SRC-1. The numbers to the left correspond to nucleotides and amino acid numbers (in brackets). The underlined methionine at the beginning of amino acid sequence is the putative translation start site. The regions of the protein rich in S and T (Ñ) and Q (ӰӰӰ) residues and the stop codon (*) are also indicated.

DESCRIPTION OF THE PREFERRED EMBODIMENTS

The present invention relates to SRC-1 polypeptides, nucleic acids encoding such polypeptides, cells, tissues and animals containing such nucleic acids, antibodies to such polypeptides, assays utilizing such polypeptides, and methods relating to all of the foregoing. A yeast two-hybrid system was used to identify proteins that interact with the activation function of the ligand-binding domain of the human progesterone receptor (hPR). A protein encoded by a 0.8 kb cDNA from a B lymphocyte cDNA expression library was found to specifically interact with the receptor in an agonist specific manner as demonstrated both in the two-hybrid system and by an in vitro interaction assay using baculovirus expressed PR. The interaction was significantly lower with ligand-free receptor or receptor bound by the antagonist RU486.

A full-length cDNA which encodes a protein with calculated mass of 114.1 kDa was isolated. Coexpression of this cDNA with hPR in mammalian cells resulted in >10 fold enhancement of the hormone-induced transcriptional activity, without altering basal activity of the promoter. In addition, it stimulates transactivation of all the steroid receptors tested, including GR (glucocorticoid), ER (estrogen), TR, RXR, and orphan receptors. Therefore, it is termed steroid receptor coactivator-one, SRC-1. SRC-1 also stimulates GAL4-VP16 and Sp1 transactivation. In contrast, the transcriptional activity of nuclear factors such as CREB and E2F was not affected. Furthermore, coexpression of SRC-1 reverses the ability of the estrogen receptor to squelch activation by hPR in a dose-dependent manner. Finally, the N-terminal truncated form of SRC-1 acts as dominant-negative repressor in steroid receptor transactivation. Taken together, our results indicate that SRC-1 encodes a coactivator required for full transactivational activity of the ligand-dependent steroid receptor superfamily.

As noted above, we have successfully used the yeast two-hybrid system to clone and identify a steroid receptor coactivator (SRC-1) protein. SRC-1 is expressed in all human tissues and cell lines analyzed as two mRNA species. A predominant single mRNA is observed in tissue from brain. With the exception of a glutamine rich region, the predicted open reading frame of 1061 amino acids does not contain an obvious transcriptional regulatory domain. SRC-1 shows higher glutamine (10.6%), serine (12.2%) and leucine (9.2%) residues than do many other proteins. The C-terminal half of SRC-1, which contains the receptor-interacting region, is relatively hydrophobic when compared to the more hydrophilic N-terminal half which has an enriched serine and threonine content.

I. Role of SRC-1 in the Multi-step Steroid Receptor Transactivation.

An assay to determine whether a protein acts as a coactivator (Dynlacht, B. D. et al., (1991), Cell 66, 563–576; Flanagan, P. M. et al., (1991), Nature 350, 436–438) indicates that SRC-1 is in fact a coactivator. First, coactivators should allow efficient activator-dependent transcription without altering basal activity (Dynlacht, B. D. et al., (1991), Cell 66, 563–576). As shown in this study, overexpression of SRC-1 in mammalian cells results in the enhancement of hPR-dependent transactivation by >10 fold without altering basal activity of the promoter. Second, a coactivator should reverse the squelching phenomenon observed when two transacting factors are present (Flanagan, P. M. et al., (1991), Nature 350, 436–438). Indeed, overexpression of hER resulted in ~19 fold reduction in hPR transactivation. Addition of SRC-1 reversed the squelching effect of hER on hPR transactivation in a dose-dependent manner, by ~16 fold. Hence, we conclude that SRC-1 is a genuine coactivator for steroid receptors. Since SRC-1 is incapable of completely reversing ER squelching of PR, it is possible that additional factor(s) also participated in concert with SRC-1 to assure full steroid receptor transactivation of target genes.

II. SRC-1 and the Role of Ligand on Steroid Receptors Transactivation.

SRC-1 appears to act as coactivator for both type A and B steroid receptors. These results suggest that SRC-1 acts at a step(s) after receptor binds to DNA. Consistent with this hypothesis, we observed that when type A receptors are overexpressed in cell lines that allow partial transactivation in the absence of hormone, presumably due to the ligand-independent activation pathway for the type A receptors (Smith, C. L. et al., (1993), Proc. Natl. Acad. Sci. USA 90, 6120–6124), SRC-1 also increased their ability to transactivate in a ligand-independent manner. The basal activity of the reporter again remained unaltered. Similarly, transactivation of type B receptors such as TR and RXR that exhibit cell-specific basal activity in the absence of ligand were also affected by SRC-1 in their ligand free state. These data further suggest that SRC-1 acts at step(s) after receptors bind to their cognate HREs. Most likely SRC-1 enhances receptor activity by facilitating receptor interaction with the basal transcriptional machinery.

The finding that SRC-1 cannot alter the antagonistic effect of RU486 on PR transactivation is an important observation. This result is consistent with our observations that SRC-1 does not interact efficiently with PR in the presence of antagonist, both in vitro and in intact cells. We and others have suggested previously that the antagonist RU486 induces a distinct conformational change in the receptor molecule that impairs the ability of receptor to transactivate, presumably due to the fact that the altered structure renders the antagonist-receptor complex unable to interact with other factors required for receptor-mediated transactivation (El-Ashry, D. et al., (1989), Mol. Endocrinol. 3, 1545–1558; Vegeto, E. et al., (1992), Cell 69, 703–713; Allan, G. F., et al., (1992a), J. Biol. Chem. 267, 19513–19520; Allan, G. F., et al., (1992b), Proc. Natl. Acad. Sci. USA 89, 11750–11754; DeMarzo, A. M. et al., (1992), Biochem. 31, 10491–10501).

Our current findings substantiate that the proper conformational change induced by agonist is necessary for receptor to interact with its coactivator, SRC-1. We postulate that the inability of antagonist-bound receptor to interact efficiently with SRC-1 leads to the biological outcome of hormonal antagonist administration to intact cells since SRC-1 appears to recognize and discriminate in favor of the agonist bound receptor complex to establish the transcriptional initiation.

III. SRC-1 is a Coactivator for the Steroid Receptor Superfamily.

The existence of cellular proteins which enhance steroid receptor transactivation have been suggested by both biochemical and genetic approaches (Meyer, M. E. et al., (1989), *Cell* 57, 433–442; Bocquel, M. T. et al., (1989), *Nucleic Acids Res.* 17, 2581–2594; Conneely, O. M. et al., (1989), "Promoter specific activating domains of the chicken progesterone receptor." In Gene Regulation by Steroid Hormones IV. A. K. Roy and J. Clark, eds. (New York, Berlin, Heidelberg, London, Paris, Tokyo: Springer-Verlag), pp. 220–223; Tasset, D. et al., (1990), *Cell* 62, 1177–1187; Shemshedini, L. et al., (1992), *J. Biol. Chem.* 261, 1834–1839; Berkenstam, A. et al., (1992), *Cell* 69, 401–412). Recent studies have identified the yeast proteins SSN6 (McDonnell, D. P. et al., (1992), *Proc. Natl. Acad. Sci. USA* 89, 10563–10567), SPT6 (Baniahmad et al., 1995), (Baniahmad C. et al. (1995), *Mol. Endocrinol.* 9, 34–43), SIN3 (Nawaz, Z. et al., (1994), *Mol. Gen. Genet.* 245, 724–733), SNF2/SWI2 (Yoshinaga, S. K. et al., (1992), *Science* 258, 1598–1604; Chiba, H. et al., (1994), *Nucleic Acids Res.* 22, 1815–1820; Laurent, B. C. et al., (1993), *Genes and Dev.* 7, 583–591) and the human homolog of hbrm protein (Muchardt, C. and Yaniv, M. (1993), *EMBO J.* 12, 4279–4290; Singh, P. et al., (1995), *Nature* 374, 562–565) as potential regulatory proteins for ER, PR and GR.

Certain of these factors are thought to function coordinately with activators to enhance transcription by affecting chromatin structure and thereby relieving the repressive effect of chromatin on gene transcription. Alterations in the nucleosome structure that affect chromatin also have been implicated in steroid-hormone action (Archer, T. K. et al., (1992), *Science* 255, 1573–1576; Schild, C. et al., (1993), *EMBO J.* 12, 423–433; Truss, M. et al., (1995), *EMBO J.* 14, 1737–1751). It is possible that these factors' effect on transactivation of steroid receptors is of an indirect nature.

Sequence analysis of the hbrm protein has revealed the presence of a conserved domain between various transcription factors, the bromodomain, which appears to be important for protein-protein interactions (Haynes, S. R. et al., (1992), *Nucleic Acids Res.* 20, 2603). In addition, it also contains a presumptive helicase domain known to be involved in chromatin decondensation during DNA replication (Laurent, B. C. et al., (1993), *Genes and Dev.* 7, 583–591). The ability of the hbrm protein to upregulate GR transactivation is dependent upon the coexpression of the Rb protein, a cell-cycle regulatory protein and again, could involve changes in chromatin structure (Singh et al., 1995). In addition, a mouse bromodomain containing protein, TIF-1 (Le Douarin, B. et al., (1995), *EMBO J.* 14, 2020–2033), the human homolog of the adaptor Sug-1, thyroid receptor interacting protein, Trip-1 (Lee et al., 1995b), as well as other Trips (Seol, W. et al., (1995), *Mol. Endocrinol.* 9, 72–85; Lee et al., 1995a), have been isolated and implicated as modulators and/or mediators of ligand-dependent steroid receptor transactivation.

Although evidence for ligand-dependent interaction has been provided for most of these proteins, no definitive evidence indicating coactivator function has been shown. Other less well characterized proteins that physically interact with ER, in a ligand-dependent manner have been described, but no functional role has been assigned (Halachmi, S. et al., (1994), *Science* 264, 1455–1458; Cavailles, V. et al, (1994), *Proc. Natl. Acad. Sci. USA* 91, 10009–10013). SRC-1 shares no significant homology to the proteins above mentioned nor does it contain similar functional canonical domains. Therefore, it is likely that the mechanism by which SRC-1 alters the rate of transcription will differ.

Although the role of SRC-1 as coactivator for steroid receptor is documented in this report, we cannot rule out potential effects on chromatin structure. Nevertheless, our evidence indicates that SRC-1 acts by direct contact with the receptor protein to modulate its activity. The ability of SRC-1 to stimulate receptor-mediated transcription and to reverse squelching between distinct steroid receptors confirms that these interactions are relevant and probably occur in vivo. The previous observation that steroid receptors can stabilize the preinitiation transcription complex (Tsai, S. Y. et al., (1990), *J. Biol. Chem.* 265, 17055–17061; Klein-Hitpass, L. et al., (1990), *Cell* 60, 247–257) lead us to speculate that SRC-1 may facilitate this process.

The finding that the N-terminal truncated form of SRC-1, which contains the receptor-interacting region, acts in a dominant-negative manner and suggests that the N-terminal region of SRC-1 is responsible for interaction(s) with the basal transcriptional machinery and/or RNA polymerase itself. These interactions represent a key regulatory event in the multi-step steroid receptor transactivation pathway.

IV. Nucleic Acid Encoding a SRC-1 Polypeptide.

Included within the scope of this invention are the functional equivalents of the herein-described isolated nucleic acid molecules. The degeneracy of the genetic code permits substitution of certain codons by other codons which specify the same amino acid and hence would give rise to the same protein. The nucleic acid sequence can vary substantially since, with the exception of methionine and tryptophan, the known amino acids can be coded for by more than one codon. Thus, portions or all of the SRC-1 gene could be synthesized to give a nucleic acid sequence significantly different from that shown in FIGS. 1A–1E. The encoded amino acid sequence thereof would, however, be preserved.

In addition, the nucleic acid sequence may comprise a nucleotide sequence which results from the addition, deletion or substitution of at least one nucleotide to the 5'-end and/or the 3'-end of the nucleic acid formula shown in FIGS. 1A–1E (SEQ ID NO:4) or a derivative thereof. Any nucleotide or polynucleotide may be used in this regard, provided that its addition, deletion or substitution does not alter the amino acid sequence of FIGS. 1A–1E (SEQ ID NO:5) which is encoded by the nucleotide sequence. For example, the present invention is intended to include any nucleic acid sequence resulting from the addition of ATG as an initiation codon at the 5'-end of the inventive nucleic acid sequence or its derivative, or from the addition of TTA, TAG or TGA as a termination codon at the 3'-end of the inventive nucleotide sequence or its derivative. Moreover, the nucleic acid molecule of the present invention may, as necessary, have restriction endonuclease recognition sites added to its 5'-end and/or 3'-end.

Such functional alterations of a given nucleic acid sequence afford an opportunity to promote secretion and/or processing of heterologous proteins encoded by foreign nucleic acid sequences fused thereto. All variations of the nucleotide sequence of the SRC-1 genes and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

V. A Nucleic Acid Probe for the Detection of SRC-1.

A nucleic acid probe of the present invention may be used to probe an appropriate chromosomal or cDNA library by usual hybridization methods to obtain another nucleic acid molecule of the present invention. A chromosomal DNA or cDNA library may be prepared from appropriate cells according to recognized methods in the art (cf. "Molecular Cloning: A Laboratory Manual", second edition, edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the amino acid sequence of the polypeptide of interest. Thus, the synthesized nucleic acid probes may be used as primers in a polymerase chain reaction (PCR) carried out in accordance with recognized PCR techniques, essentially according to PCR Protocols, "A Guide to Methods and Applications", edited by Michael et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (cf. "Molecular Cloning: A Laboratory Manual", second edition, edited by Sambrook, Fritsch, & Maniatis, Cold Spring Harbor Laboratory, 1989). The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA, as well as DNA probes, such probes being generated using techniques known in the art. The nucleic acid probe may be immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

VI. A Probe Based Method and Kit for Detecting SRC-1.

One method of detecting the presence of SRC-1 in a sample comprises a) contacting said sample with the above-described nucleic acid probe, under conditions such that hybridization occurs, and b) detecting the presence of said probe bound to said nucleic acid molecule. One skilled in the art would select the nucleic acid probe according to techniques known in the an as described above. Samples to be tested include but should not be limited to RNA samples of human tissue.

A kit for detecting the presence of SRC-1 in a sample comprises at least one container means having disposed therein the above-described nucleic acid probe. The kit may further comprise other containers comprising one or more of the following: wash reagents and reagents capable of detecting the presence of bound nucleic acid probe. Examples of detection reagents include, but are not limited to radiolabelled probes, enzymatic labeled probes (horseradish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like. One skilled in the art will readily recognize that the nucleic acid probes described in the present invention can readily be incorporated into one of the established kit formats which are well known in the art.

VII. DNA Constructs Comprising a SRC-1 Nucleic Acid Molecule and Cells Containing These Constructs.

The present invention also relates to a recombinant DNA molecule comprising, 5' to 3', a promoter effective to initiate transcription in a host cell and the above-described nucleic acid molecules. In addition, the present invention relates to a recombinant DNA molecule comprising a vector and an above-described nucleic acid molecules. The present invention also relates to a nucleic acid molecule comprising a transcriptional region functional in a cell, a sequence complimentary to an RNA sequence encoding an amino acid sequence corresponding to the above-described polypeptide, and a transcriptional termination region functional in said cell. The above-described molecules may be isolated and/or purified DNA molecules.

The present invention also relates to a cell or organism that contains an above-described nucleic acid molecule. The peptide may be purified from cells which have been altered to express the peptide. A cell is said to be "altered to express a desired peptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding an SRC-1 gene may be obtained by the above-described methods. This region may be retained for its transcriptional termination regulatory sequences, such as termination and polyadenylation. Thus, by retaining the 3'-region naturally contiguous to the DNA sequence encoding an SRC-1 gene, the transcriptional termination signals may be provided. Where the transcriptional termination signals are not satisfactorily functional in the expression host cell, then a 3' region functional in the host cell may be substituted.

Two DNA sequences (such as a promoter region sequence and an SRC-1 sequence) are said to be operably linked if the nature of the linkage between the two DNA sequences does not (1) result in the introduction of a frame-shift mutation, (2) interfere with the ability of the promoter region sequence to direct the transcription of an SRC-1 gene sequence, or (3) interfere with the ability of the an SRC-1 gene sequence to be transcribed by the promoter region sequence. Thus, a promoter region would be operably linked to a DNA sequence if the promoter were capable of effecting transcription of that DNA sequence. Thus, to express an SRC-1 gene, transcriptional and translational signals recognized by an appropriate host are necessary.

The present invention encompasses the expression of the SRC-1 gene (or a functional derivative thereof) in either prokaryotic or eukaryotic cells. Prokaryotic hosts are, generally, very efficient and convenient for the production of recombinant proteins and are, therefore, one type of preferred expression system for the SRC-1 gene. Prokaryotes most frequently are represented by various strains of *E. coli*. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include γgt10, γgt11 and the like; and suitable virus vectors may include pMAM-neo, pKRC and the like. Preferably, the selected vector of the present invention has the capacity to replicate in the selected host cell.

Recognized prokaryotic hosts include bacteria such as *E. coil*, Bacillus, Streptomyces, Pseudomonas, Salmonella, Serratia, and the like. However, under such conditions, the peptide will not be glycosylated. The prokaryotic host must be compatible with the replicon and control sequences in the expression plasmid.

To express SRC-1 (or a functional derivative thereof) in a prokaryotic cell, it is necessary to operably link the SRC-1 sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, lacZ, lacI, and gal promoters of *E. coli*, the α-amylase (Ulmanen et at., *J. Bacteriol*. 162:176–182 (1985)) and the ç-28-specific promoters of *B. subtilis* (Gilman et al., Gene sequence 32:11–20(1984)), the promoters of the bacteriophages of Bacillus (Gryczan, In: The Molecular Biology of the Bacilli, Academic Press, Inc., New York (1982)), and Streptomyces promoters (Ward et al., *Mol. Gen. Genet*. 203:468–478(1986)). Prokaryotic promoters are reviewed by Glick (*J. Ind. Microbiot*. 1:277–282 (1987)); Cenatiempo (*Biochimie* 68:505–516(1986)); and Gottesman (*Ann. Rev. Genet*. 18:415–442 (1984)).

Proper expression in a prokaryotic cell also requires the presence of a ribosome binding site upstream of the gene sequence-encoding sequence. Such ribosome binding sites are disclosed, for example, by Gold et al. (*Ann. Rev. Microbiol*. 35:365–404(1981)). The selection of control sequences, expression vectors, transformation methods, and the like, are dependent on the type of host cell used to express the gene. As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the SRC-1 peptide of interest. Thus, any primary human cell line such as those found in an ATTC catalogue can be utilized. Suitable hosts may often include eukaryotic cells. Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO or CHO-K1, or cells of lymphoid origin and their derivatives. Preferred mammalian host cells include SP2/0 and J558L, which may provide better capacities for correct post-translational processing.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the Drosophila larvae. Using insect cells as hosts, the Drosophila alcohol dehydrogenase promoter can be used. Rubin, *Science* 240:1453–1459(1988). Alternatively, baculovirus vectors can be engineered to express large amounts of SRC-1 in insects cells (Jasny, *Science* 238:1653 (1987); Miller et al., In: Genetic Engineering (1986), Setlow, J. K., et al., eds., Plenum, Vol. 8, pp. 277–297).

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals. Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., prepeptides). For a mammalian host, several possible vector systems are available for the expression of SRC-1.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, papovavirus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation. Other regulatory signals which may be utilized are described in U.S. Pat. No. 5,364,791 and in U.S. patent application Ser. No. 07/939,246, filed Sep. 2, 1993, both of which are incorporated herein by reference in their entirety including any drawings.

Expression of SRC-1 in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol Appl. Gen.* 1:273–288(1982)); the TK promoter of Herpes virus (McKnight, *Cell* 31:355–365 (1982)); the SV40 early promoter (Benoist et al., *Nature* (London) 290:304–310(1981)); the yeast gal4 gene sequence promoter (Johnston et al., *Proc. Natl. Acad. Sci.* (*USA*) 79:6971–6975(1982); Silver et al., *Proc. Natl. Acad. Sci.* (*USA*) 81:5951–5955 (1984)).

Translation of eukaryotic mRNA is initiated at the codon which encodes the first methionine. For this reason, it is preferable to ensure that the linkage between a eukaryotic promoter and a DNA sequence which encodes SRC-1 (or a functional derivative thereof) does not contain any intervening codons which are capable of encoding a methionine (i.e., AUG). The presence of such codons results either in a formation of a fusion protein (if the AUG codon is in the same reading frame as the SRC-1 coding sequence) or a frame-shift mutation (if the AUG codon is not in the same reading frame as the SRC-1 coding sequence).

A SRC-1 nucleic acid molecule and an operably linked promoter may be introduced into a recipient prokaryotic or eukaryotic cell either as a nonreplicating DNA (or RNA) molecule, which may either be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, *Molec. Cell. Biol.* 3:280(1983).

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coil* (such as, for example, pBR322, ColEl, pSC101, pACYC 184, ΠVX. Such plasmids are, for example, disclosed by Sambrook (cf. "Molecular Cloning: A Laboratory Manual", second edition, edited by Sambrook, Fritsch, & Maniatis, Cold Spring Harbor Laboratory, (1989)). Bacillus plasmids include pC194, pC221, pT127, and the like. Such plasmids are disclosed by Gryczan (In: The Molecular Biology of the Bacilli, Academic Press, New York (1982), pp. 307–329). Suitable Streptomyces plasmids include p1J101 (Kendall et al., *J. Bacteriol.* 169:4177–4183 (1987)), and streptomyces bacteriophages such as ΦC31 (Chater et al., In: Sixth International Symposium on Actinomycetales Biology, Akademiai Kaido, Budapest, Hungary (1986), pp. 45–54). Pseudomonas plasmids are reviewed by John et al. (*Rev. Infect. Dis.* 8:693–704(1986)), and Izaki (*Jpn. J. Bacteriol.* 33:729–742 (1978)).

Preferred eukaryotic plasmids include, for example, BPV, vaccinia, SV40, 2-micron circle, adenovirus, retrovirus, and the like, or their derivatives. Such plasmids are well known in the art (Botstein et al., *Miami Wntr. Symp.* 19:265–274 (1982); Broach, In: "The Molecular Biology of the Yeast Saccharomyces: Life Cycle and Inheritance", Cold Spring Harbor Laboratory, Cold Spring Harbor, N.Y., p. 445–470 (1981); Broach, *Cell* 28:203–204 (1982); Bollon et at., *J. Ctin. Hematol. Oncol.* 10:39–48 (1980); Maniatis, In: *Cell Biology: A Comprehensive Treatise, Vol.* 3, Gene Sequence Expression, Academic Press, New York, pp. 563–608(1980).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of SRC-1 or fragments thereof. This can take place in the transformed cells as such, or following the induction of these cells to differentiate (for example, by administration of bromodeoxyuracil to neuroblastoma cells or the like). A variety of incubation conditions can be used to form the peptide of the present invention. The most preferred conditions are those which mimic physiological conditions.

VIII. Purified SRC-1 Polypeptides

In another aspect the invention features an isolated, enriched, or purified SRC-1 polypeptide.

By "isolated" in reference to a polypeptide is meant a polymer of 2 (preferably 7, more preferably 13, most prefereably 25) or more amino acids conjugated to each other, including polypeptides that are isolated from a natural source or that are synthesized. In certain aspects longer polypeptides are preferred, such as those with 402, 407, 413, or 425 contiguous amino acids set forth in FIGS. 1A–1E. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is essentially free (about 90–95% pure at least) of non-amino acid material naturally associated with it.

By the use of the term "enriched" in reference to a polypeptide is meant that the specific amino acid sequence constitutes a significantly higher fraction (2–5 fold) of the total of amino acids present in the cells or solution of interest than in normal or diseased cells or in the cells from which the sequence was taken. This could be caused by a person by preferential reduction in the amount of other amino acids present, or by a preferential increase in the amount of the specific amino acid sequence of interest, or by a combination of the two. However, it should be noted that enriched does not imply that there are no other amino acid sequences present, just that the relative amount of the sequence of interest has been significantly increased. The term significant here is used to indicate that the level of increase is useful to the person making such an increase, and generally means an increase relative to other amino acids of about at least 2 fold, more preferably at least 5 to 10 fold or even more. The term also does not imply that there is no amino acid from other sources. The other source amino acid may, for example, comprise amino acid encoded by a yeast or bacterial genome, or a cloning vector such as pUC19. The term is meant to cover only those situations in which man has intervened to elevate the proportion of the desired nucleic acid.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment (compared to the natural level this level should be at least 2–5 fold greater, e.g., in terms of mg/ml). Purification of at least one order of magnitude, preferably two or three orders, and more preferably four or five orders of magnitude is expressly contemplated. The substance is preferably free of contamination at a functionally significant level, for example 90%, 95%, or 99% pure.

In preferred embodiments the SRC-1 polypeptide contains at least 25, 30, 35, 40, 50, 425, 430, 435, 440, or 450 contiguous amino acids of the full-length sequence set forth in FIGS. 1A–1E, or a functional derivative thereof.

In another aspect, the invention describes a polypeptide comprising a recombinant SRC-1 polypeptide or a unique fragment thereof. By "unique fragment," is meant an amino acid sequence present in a full-length SRC-1 polypeptide that is not present in any other naturally occurring polypeptide. Preferably, such a sequence comprises 6 contiguous amino acids present in the full sequence. More preferably, such a sequence comprises 12 contiguous amino acids present in the full sequence. Even more preferably, such a sequence comprises 18 contiguous amino acids present in the full sequence.

By "recombinant SRC-1 polypeptide" is meant to include a polypeptide produced by recombinant DNA techniques such that it is distinct from a naturally occurring polypeptide either in its location (e.g., present in a different cell or tissue than found in nature), purity or structure. Generally, such a recombinant polypeptide will be present in a cell in an amount different from that normally observed in nature.

A variety of methodologies known in the art can be utilized to obtain the peptide of the present invention. The peptide may be purified from tissues or cells which naturally produce the peptide. Alternatively, the above-described isolated nucleic acid fragments could be used to expressed the SRC-1 protein in any organism. The samples of the present invention include cells, protein extracts or membrane extracts of cells, or biological fluids. The sample will vary based on the assay format, the detection method and the nature of the tissues, cells or extracts used as the sample.

Any eukaryotic organism can be used as a source for the peptide of the invention, as long as the source organism naturally contains such a peptide. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the peptide free of natural contaminants. These include, but are not limited to: size-exclusion chromatography, HPLC, ion-exchange chromatography, and immuno-affinity chromatography.

IX. An Antibody Having Binding Affinity to a SRC-1 Polypeptide and a Hybridoma Containing the Antibody.

In yet another aspect the invention features an antibody (e.g., a monoclonal or polyclonal antibody) having specific binding affinity to a SRC-1 polypeptide. The antibody contains a sequence of amino acids that is able to specifically bind to a SRC-1 polypeptide. By "specific binding affinity" is meant that the antibody binds to SRC-1 polypeptides with greater affinity than it binds to other polypeptides under specified conditions.

Antibodies having specific binding affinity to a SRC-1 polypeptide may be used in methods for detecting the presence and/or amount of a SRC-1 polypeptide in a sample by contacting the sample with the antibody under conditions such that an immunocomplex forms and detecting the presence and/or amount of the antibody conjugated to the SRC-1 polypeptide. Diagnostic kits for performing such methods may be constructed to include a first container means containing the antibody and a second container means having a conjugate of a binding partner of the antibody and a label.

In another aspect the invention features a hybridoma which produces an antibody having specific binding affinity to a SRC-1 polypeptide. By "hybridoma" is meant an immortalized cell line which is capable of secreting an antibody, for example a SRC-1 antibody. In preferred embodiments the SRC-1 antibody comprises a sequence of amino acids that is able to specifically bind a SRC-1 polypeptide.

The present invention relates to an antibody having binding affinity to a SRC-1 polypeptide. The polypeptide may have the amino acid sequence set forth in FIGS. 1A–1E (SEQ ID NO:5), or functional derivative thereof, or at least 9 contiguous amino acids thereof (preferably, at least 20, 30, 35, or 40 contiguous amino acids thereof).

The present invention also relates to an antibody having specific binding affinity to an SRC-1 polypeptide. Such an antibody may be isolated by comparing its binding affinity to a SRC-1 polypeptide with its binding affinity to another polypeptide. Those which bind selectively to SRC-1 would be chosen for use in methods requiring a distinction between SRC-1 and other polypeptides. Such methods could include, but should not be limited to, the analysis of altered SRC-1 expression in tissue containing other polypeptides.

The SRC-1 proteins of the present invention can be used in a variety of procedures and methods, such as for the generation of antibodies, for use in identifying pharmaceutical compositions, and for studying DNA/protein interaction.

The SRC-1 peptide of the present invention can be used to produce antibodies or hybridomas. One skilled in the art will recognize that if an antibody is desired, such a peptide would be generated as described herein and used as an immunogen. The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting. The present invention also relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands (1984); St. Groth et al., *J. Immunol. Methods* 35:1–21(1980)). Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Agl4 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)). Hybridomas secreting the desired antibodies are cloned and the class and subclass is determined using procedures known in the art (Campbell, "Monoclonal Antibody Technology: Laboratory Techniques in Biochemistry and Molecular Biology", supra (1984)).

For polyclonal antibodies, antibody containing antisera is isolated from the immunized animal and is screened for the presence of antibodies with the desired specificity using one of the above-described procedures. The above-described antibodies may be detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Stemberger et al., *J. Histochem. Cytochem.* 18:315 (1970); Bayer et al., *Meth. Enzym.* 62:308 (1979); Engval et al.,*Immunot.* 109:129(1972); Goding,*J. Immunol. Meth.* 13:215(1976)). The labeled antibodies of the present invention can be used for in vitro, in vivo, and in situ assays to identify cells or tissues which express a specific peptide.

The above-described antibodies may also be immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10(1986); Jacoby et al., *Meth. Enzym.* 34, Academic Press, New York (1974)). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In Synthetic Peptides, A User's Guide, W.H. Freeman, New York, pp. 289–307(1992), and Kaspczak et al., Biochemistry 28:9230–8(1989).

Anti-peptide peptides can be generated by replacing the basic amino acid residues found in the SRC-1 peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

X. An Antibody Based Method and Kit for Detecting SRC-1.

The present invention encompasses a method of detecting an SRC-1 polypeptide in a sample, comprising: a) contacting the sample with an above-described antibody, under conditions such that immunocomplexes form, and b) detecting the presence of said antibody bound to the polypeptide. In detail, the methods comprise incubating a test sample with one or more of the antibodies of the present invention and assaying whether the antibody binds to the test sample. Altered levels of SRC-1 in a sample as compared to normal levels may indicate disease.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques" Elsevier Science Publishers, Amsterdam, The Netherlands (1986); Bullock et al., "Techniques in Immunocytochemistry," Academic Press, Orlando, Fla. Vol. 1(1982), Vol. 2 (1983), Vol. 3 (1985); Tijssen, "Practice and Theory of Enzyme Immunoassays: Laboratory Techniques in Biochemistry and Molecular Biology," Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

A kit contains all the necessary reagents to carry out the previously described methods of detection. The kit may comprise: i) a first container means containing an above-described antibody, and ii) second container means containing a conjugate comprising a binding partner of the antibody and a label. In another preferred embodiment, the kit further comprises one or more other containers comprising one or more of the following: wash reagents and reagents capable of detecting the presence of bound antibodies.

Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits. One skilled in the art will readily recognize that the antibodies described in the present invention can readily be incorporated into one of the established kit formats which are well known in the art.

XI. Isolation of Compounds which Interact with SRC-1.

The present invention also relates to a method of detecting a compound capable of binding to a SRC-1 polypeptide comprising incubating the compound with SRC-1 and detecting the presence of the compound bound to SRC-1. The compound may be present within a complex mixture, for example, serum, body fluid, or cell extracts.

The present invention also relates to a method of detecting an agonist or antagonist of SRC-1 activity comprising incubating cells that produce SRC-1 in the presence of a compound and detecting changes in the level of SRC-1 activity. The compounds thus identified would produce a change in activity indicative of the presence of the compound. The compound may be present within a complex mixture, for example, serum, body fluid, or cell extracts. Once the compound is identified it can be isolated using techniques well known in the art.

The present invention also encompasses a method of agonizing (stimulating) or antagonizing SRC-1 associated activity in a mammal comprising administering to said mammal an agonist or antagonist to SRC-1 in an amount sufficient to effect said agonism or antagonism. A method of treating diseases in a mammal with an agonist or antagonist of SRC-1 activity comprising administering the agonist or antagonist to a mammal in an amount sufficient to agonize or antagonize SRC-1 associated functions is also encompassed in the present application.

XII. Transgenic Animals.

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division (Brinster et al., *Proc. Nat. Acad. Sci. USA* 82: 4438–4442 (1985)). Embryos can be infected with viruses, especially retroviruses, modified to carry inorganic-ion receptor nucleotide sequences of the invention.

Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), Harlan Sprague-Dawley (Indianapolis, Ind.), etc.

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, *Experientia* 47: 897–905 (1991). Other procedures for introduction of DNA into tissues of animals are described in U.S. Pat. No., 4,945,050 (Sandford et al., Jul. 30, 1990).

By way of example only, to prepare a transgenic mouse, female mice are induced to superovulate. Females are placed with males, and the mated females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer et al., *Cell* 63:1099–1112 (1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. See, for example, *Teratocarcinomas and Embryonic Stem Cells, A Practical Approach*, E. J. Robertson, ed., IRL Press (1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination. Capecchi, *Science* 244: 1288–1292 (1989). Methods for positive selection of the recombination event (i.e., neo resistance) and dual positive-negative selection (i.e., neo resistance and gancyclovir resistance) and the subsequent identification of the desired clones by PCR have been described by Capecchi, supra and Joyner et al., *Nature* 338: 153–156 (1989), the teachings of which are incorporated herein. The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene. Procedures for the production of non-rodent mammals and other animals have been discussed by others. See Houdebine and Chourrout, supra; Pursel et al., *Science* 244:1281–1288 (1989); and Simms et al., *Bio/Technology* 6:179–183 (1988).

XIII. Gene Therapy

SRC-1 or its genetic sequences will also be useful in gene therapy (reviewed in Miller, *Nature* 357:455–460, (1992). Miller states that advances have resulted in practical approaches to human gene therapy that have demonstrated positive initial results. The basic science of gene therapy is described in Mulligan, *Science* 260:926–931, (1993).

In one preferred embodiment, an expression vector containing the SRC-1 coding sequence is inserted into cells, the cells are grown in vitro and then infused in large numbers into patients. In another preferred embodiment, a DNA segment containing a promoter of choice (for example a strong promoter) is transferred into cells containing an endogenous SRC-1 in such a manner that the promoter segment enhances expression of the endogenous SRC-1 gene (for example, the promoter segment is transferred to the cell such that it becomes directly linked to the endogenous SRC-1 gene).

The gene therapy may involve the use of an adenovirus containing SRC-1 cDNA targeted to a tumor, systemic SRC-1 increase by implantation of engineered cells, injection with SRC-1 virus, or injection of naked SRC-1 DNA into appropriate tissues.

Target cell populations may be modified by introducing altered forms of one or more components of the protein complexes in order to modulate the activity of such complexes. For example, by reducing or inhibiting a complex component activity within target cells, an abnormal signal transduction event(s) leading to a condition may be decreased, inhibited, or reversed. Deletion or missense mutants of a component, that retain the ability to interact with other components of the protein complexes but cannot function in signal transduction may be used to inhibit an abnormal, deleterious signal transduction event.

Expression vectors derived from viruses such as retroviruses, vaccinia virus, adenovirus, adeno-associated virus, herpes viruses, several RNA viruses, or bovine papilloma virus, may be used for delivery of nucleotide sequences (e g., cDNA) encoding recombinant SRC-1 protein into the targeted cell population (e.g., tumor cells). Methods which are well known to those skilled in the art can be used to construct recombinant viral vectors containing coding sequences. See, for example, the techniques described in Maniatis et al., *Molecular Cloning: A Laboratory Manual*, Cold Spring Harbor Laboratory, N.Y. (1989), and in Ausubel et al., *Current Protocols in Molecular Biology*, Greene Publishing Associates and Wiley Interscience, N.Y. (1989). Alternatively, recombinant nucleic acid molecules encoding protein sequences can be used as naked DNA or in reconstituted system e.g., liposomes or other lipid systems for delivery to target cells (See e.g., Felgner et al., *Nature* 337:387–8, 1989). Several other methods for the direct transfer of plasmid DNA into cells exist for use in human gene therapy and involve targeting the DNA to receptors on cells by complexing the plasmid DNA to proteins. See, Miller, supra.

In its simplest form, gene transfer can be performed by simply injecting minute amounts of DNA into the nucleus of a cell, through a process of microinjection. Capecchi M R, *Cell* 22:479–88 (1980). Once recombinant genes are introduced into a cell, they can be recognized by the cells normal mechanisms for transcription and translation, and a gene product will be expressed. Other methods have also been attempted for introducing DNA into larger numbers of cells. These methods include: transfection, wherein DNA is precipitated with $CaPO_4$ and taken into cells by pinocytosis (Chen C. and Okayama H, *Mol. Cell Biol.* 7:2745–52 (1987)); electroporation, wherein cells are exposed to large voltage pulses to introduce holes into the membrane (Chu G. et al., *Nucleic Acids Res.*, 15:1311–26 (1987)); lipofection/liposome fusion, wherein DNA is packaged into lipophilic vesicles which fuse with a target cell (Felgner P L., et al., *Proc. Natl. Acad. Sci. USA*. 84:7413–7 (1987)); and particle bombardment using DNA bound to small projectiles (Yang N S. et al., *Proc. Natl. Acad. Sci.* 87:9568–72 (1990)). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. Curiel D T et al., *Am. J. Respir. Cell. Mol. Biol.*, 6:247–52 (1992).

As used herein "gene transfer" means the process of introducing a foreign nucleic acid molecule into a cell. Gene transfer is commonly performed to enable the expression of a particular product encoded by the gene. The product may include a protein, polypeptide, anti-sense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In another preferred embodiment, a vector having nucleic acid sequences encoding SRC-1 is provided in which the nucleic acid sequence is expressed only in specific tissue. Methods of achieving tissue-specific gene expression as set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid sequence which is capable of being expressed in vivo in an animal and thereby providing or augmenting the function of an endogenous gene which is missing or defective in the animal.

The nucleic acid sequence encoding SRC-1 can be administered prophylactically, or to patients having a disorder listed above, e.g., by exogenous delivery of the nucleic acid sequence encoding SRC-1 as naked DNA, DNA associated with specific carriers, or in a nucleic acid expression vector to a desired tissue by means of an appropriate delivery vehicle, e.g., a liposome, by use of iontophoresis, electroporation and other pharmacologically approved methods of delivery. Routes of administration may include intramuscular, intravenous, aerosol, oral (tablet or pill form), topical, systemic, ocular, as a suppository, intraperitoneal and/or intrathecal.

Some methods of delivery that may be used include:

a. encapsulation in liposomes, b. transduction by retroviral vectors, c. localization to nuclear compartment utilizing nuclear targeting site found on most nuclear proteins, d. transfection of cells ex vivo with subsequent reimplantation or administration of the transfected cells, e. a DNA transporter system.

A SRC-1 nucleic acid sequence may be administered utilizing an ex vivo approach whereby cells are removed from an animal, transduced with the SRC-1 nucleic acid sequence and reimplanted into the animal. The liver can be accessed by an ex vivo approach by removing hepatocytes from an animal, transducing the hepatocytes in vitro with the SRC-1 nucleic acid sequence and reimplanting them into the animal (e.g., as described for rabbits by Chowdhury et al, Science 254: 1802–1805, 1991, or in humans by Wilson, Hum. Gene Ther. 3: 179–222, 1992) incorporated herein by reference.

Many nonviral techniques for the delivery of a SRC-1 nucleic acid sequence into a cell can be used, including direct naked DNA uptake (e.g., Wolff et al., Science 247: 1465–1468, 1990), receptor-mediated DNA uptake, e.g., using DNA coupled to asialoorosomucoid which is taken up by the asialoglycoprotein receptor in the liver (Wu and Wu, J. Biol. Chem. 262: 4429–4432, 1987; Wu et al., J. Biol. Chem. 266: 14338–14342, 1991), and liposome-mediated delivery (e.g., Kaneda et al., Expt. Cell Res. 173: 56–69, 1987; Kaneda et al., Science 243: 375–378, 1989; Zhu et al., Science 261: 209–211, 1993). Many of these physical methods can be combined with one another and with viral techniques; enhancement of receptor-mediated DNA uptake can be effected, for example, by combining its use with adenovirus (Curiel et al., Proc. Natl. Acad. Sci. USA 88: 8850–8854, 1991; Cristiano et al., Proc. Natl. Acad. Sci. USA 90: 2122–2126, 1993).

The SRC-1 or nucleic acid encoding a SRC-1 polypeptide or protein may also be administered via an implanted device that provides a support for growing cells. Thus, the cells may remain in the implanted device and still provide the useful and therapeutic agents of the present invention.

The term "protein" refers to a compound formed of 5–50 or more amino acids joined together by peptide bonds. An "amino acid" is a subunit that is polymerized to form proteins and there are twenty amino acids that are universally found in proteins. The general formula for an amino acid is $H_2N—CHR—COOH$, in which the R group can be anything from a hydrogen atom (as in the amino acid glycine) to a complex ring (as in the amino acid tryptophan).

XV. Derivatives

Also provided herein are functional derivatives of SRC-1. By "functional derivative" is meant a "chemical derivative," "fragment," "variant," "chimera," or "hybrid", which terms are defined below. A functional derivative retains at least a portion of the function of the protein, for example reactivity with an antibody specific for the complex, enzymatic activity or binding activity mediated through noncatalytic domains, which permits its utility in accordance with the present invention.

A "chemical derivative" contains additional chemical moieties not normally a part of the protein. Covalent modifications of the protein or peptide are included within the scope of this invention. Such modifications may be introduced into the molecule by reacting targeted amino acid residues of the peptide with an organic derivatizing agent that is capable of reacting with selected side chains or terminal residues, as described below.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect or reversing the charge of the lysinyl residues. Other suitable reagents for derivatizing primary amine containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine alpha-amino group.

Tyrosyl residues are well-known targets of modification for introduction of spectral labels by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction carbodiimide (R'-N-C-N-R') such as 1-cyclohexyl-3-(2-morpholinyl(4-ethyl) carbodiimide or 1-ethyl-3-(4-azonia-4,4-dimethylpentyl) carbodiimide. Furthermore, aspartyl and glutamyl residue are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful, for example, for cross-linking the peptide to a water-insoluble support matrix or to other macromolecular carriers. Commonly used cross-linking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[pazidophenyl)dithiolpropioimidate yield photo-activatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, T. E., Proteins: Structure and Molecular Properties, W.H. Freeman & Co., San Francisco, pp. 79–86 (1983)), acetylation of the N-terminal amine, and, in some instances, amidation of the C-terminal carboxyl groups.

Such derivatized moieties may improve the stability, solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences*, 18th ed., Mack Publishing Co., Easton, Pa. (1990).

The term "fragment" is used to indicate a polypeptide derived from the amino acid sequence of the protein having a length less than the full-length polypeptide from which it has been derived. Such a fragment may, for example, be produced by proteolytic cleavage of the full-length protein. Preferably, the fragment is obtained recombinantly by appropriately modifying the DNA sequence encoding the proteins to delete one or more amino acids at one or more sites of the C-terminus, N-terminus, and/or within the native sequence. It is understood that such fragments, may retain one or more characterizing portions of the native protein. Examples of such retained characteristics include: catalytic activity; substrate specificity; interaction with other molecules in the intact cell; regulatory functions; or binding with an antibody specific for the native protein, or an epitope thereof.

Another functional derivative intended to be within the scope of the present invention is a "variant" polypeptide which either lack one or more amino acids or contain additional or substituted amino acids relative to the native polypeptide. The variant may be derived from a naturally occurring protein by appropriately modifying the protein DNA coding sequence to add, remove, and/or to modify codons for one or more amino acids at one or more sites of the C-terminus, N-terminus, and/or within the native sequence. It is understood that such variants having added, substituted and/or additional amino acids retain one or more characterizing portions of the native protein, as described above.

A functional derivative of a protein with deleted, inserted and/or substituted amino acid residues may be prepared using standard techniques well-known to those of ordinary skill in the art. For example, the modified proteins may be produced using site-directed mutagenesis techniques (as exemplified by Adelman et al., 1983, DNA 2:183) wherein nucleotides in the DNA coding the sequence are modified such that a modified coding sequence is modified, and thereafter expressing this recombinant DNA in a prokaryotic or eukaryotic host cell, using techniques such as those described above. Alternatively, proteins with amino acid deletions, insertions and/or substitutions may be conveniently prepared by direct chemical synthesis, using methods well-known in the art. The functional derivatives typically exhibit the same qualitative biological activity as the native proteins.

XVI Administration

Administration as used herein refers to the route of introduction of a vector or carrier of DNA into the body. Administration may include intravenous, intramuscular, topical, or oral methods of delivery. Administration can be directly to a target tissue or through systemic delivery.

In particular, the present invention can be used for treating disease or for administering the formulated DNA expression vectors capable of expressing any specific nucleic acid sequence. Administration can also include administering a regulatable vector discussed above. Such administration of a vector can be used to treat disease. The preferred embodiment is by direct injection to the target tissue or systemic administration.

A second critical step is the delivery of the DNA vector to the nucleus of the target cell where it can express a gene product. In the present invention this is accomplished by formulation. The formulation can consist of purified DNA vectors or DNA vectors associated with other formulation elements such as lipids, proteins, carbohydrates, synthetic organic or inorganic compounds. Examples of such formulation elements include, but are not limited to, lipids capable of forming liposomes, cationic lipids, hydrophilic polymers, polycations (e.g., protamine, polybrene, spermidine, polylysine), peptide or synthetic ligands recognizing receptors on the surface of the target cells, peptide or synthetic ligands capable of inducing endosomal lysis, peptide or synthetic ligands capable of targeting materials to the nucleus, gels, slow release matrices, soluble or insoluble particles, as well as other formulation elements not listed. This includes formulation elements for enhancing the delivery, uptake, stability, and/or expression of genetic material into cells.

The delivery and formulation of any selected vector construct will depend on the particular use for the expression vectors. In general, a specific formulation for each vector construct used will focus on vector uptake with regard to the particular targeted tissue, followed by demonstration of efficacy. Uptake studies will include uptake assays to evaluate cellular uptake of the vectors and expression of the tissue specific DNA of choice. Such assays will also determine the localization of the target DNA after uptake, and establishing the requirements for maintenance of steady-state concentrations of expressed protein. Efficacy and cytotoxicity can then be tested. Toxicity will not only include cell viability but also cell function.

DNA uptake by cells associated with fluid spaces have the unique ability to take up DNA from the extracellular space after simple injection of purified DNA preparations into the fluid spaces. Expression of DNA by this method can be sustained for several months.

Incorporating DNA by formulation into particulate complexes of nanometer size that undergo endocytosis increases the range of cell types that will take up foreign genes from the extracellular space.

Formulation can also involve DNA transporters which are capable of forming a non-covalent complex with DNA and directing the transport of the DNA through the cell membrane. This may involve the sequence of steps including endocytosis and enhanced endosomal release. It is preferable that the transporter also transport the DNA through the nuclear membrane. See, e.g., the following applications all of which (including drawings) are hereby incorporated by reference herein: (1) Woo et al., U.S. Ser. No. 07/855,389, entitled "A DNA Transporter System and Method of Use" filed Mar. 20, 1992; (2) Woo et al., PCT/US93/02725, entitled "A DNA Transporter System and method of Use", (designating the U.S. and other countries) filed Mar. 19, 1993; and (3) continuation-in-part application by Woo et al., entitled "Nucleic Acid Transporter Systems and Methods of Use", filed Dec. 14, 1993, assigned attorney docket number 205/012 but not yet assigned a U.S. Serial Number.

In addition, delivery can be cell specific or tissue specific by including cell or tissue specific promoters. Furthermore, mRNA stabilizing sequences (3' UTR's) can be used to provide stabilized modified receptor molecules. Such stabilizing sequences increase the half-life of mRNAs and can be cell or tissue specific. The above is discussed in more detail in U.S. Pat. No. 5,298,422 (Schwartz et al.) and U.S. application Ser. No. 08/209,846 (Schwartz et al.), filed Mar. 9, 1994, entitled "Expression Vector Systems and Method of Use." Both of these, the whole of which, are incorporated by reference herein, including drawings. Information regarding endothelial specific sequences is provided in U.S. patent application Ser. No. 08/146,930, filed Nov. 1, 1993 and Ser. No. 08/147,777, filed Nov. 1, 1993 both of which are incorporated herein by reference in their entirety including any drawings. Information regarding muscle specific sequences is provided in U.S. patent application Ser. No. 08/472,809.

In a preferred method of administration involving a DNA transporter system, the DNA transporter system has a DNA binding complex with a binding molecule capable of non-covalently binding to DNA which is covalently linked to a surface ligand. The surface ligand is capable of binding to a cell surface receptor and stimulating entry into the cell by endocytosis, pinocytosis, or potocytosis. In addition, a second DNA binding complex is capable of non-covalently binding to DNA and is covalently linked to a nuclear ligand. The nuclear ligand is capable of recognizing and transporting a transporter system through a nuclear membrane. Additionally, a third DNA binding complex may be used which is also capable of non-covalently binding to DNA. The third binding molecule is covalently linked to an element that induces endosomal lysis or enhanced release of the complex from the endosome after endocytosis. The binding molecules can be spermine, spermine derivatives, histones, cationic peptides and/or polylysine. See also Szoka, C. F., Jr. et al., Bioconjug. Chem. 4:85–93 (1993); Szoka, F. C., Jr. et al., P.N.A.S., 90:893–897 (1993).

Transfer of genes directly has been very effective. Experiments show that administration by direct injection of DNA into joint tissue results in expression of the gene in the area of injection. Injection of plasmids containing the mutated receptors into the spaces of the joints results in expression of the gene for prolonged periods of time. The injected DNA appears to persist in an unintegrated extrachromosomal state. This means of transfer is the preferred embodiment.

The formulation used for delivery may also be by liposomes or cationic lipids. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acid remains biologically active. Cationic lipid formulations such as formulations incorporating DOTMA has been shown to deliver DNA expression vectors to cells yielding production of the corresponding protein. Lipid formulations may be non-toxic and biodegradable in composition. They display long circulation half-lives and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system. See Szoka, F. C., Jr. et al., Pharm. Res., 7:824–834 (1990); Szoka, F. C., Jr. et al., Pharm. Res., 9:1235–1242 (1992).

The chosen method of delivery should result in nuclear or cytoplasmic accumulation and optimal dosing. The dosage will depend upon the disease and the route of administration but should be between 1–1000 μg/kg of body weight. This level is readily determinable by standard methods. It could be more or less depending on the optimal dosing. The duration of treatment will extend through the course of the disease symptoms, possibly continuously. The number of doses will depend upon disease, the formulation and efficacy data from clinical trials.

With respect to vectors, the pharmacological dose of a vector and the level of gene expression in the appropriate cell type includes but is not limited to sufficient protein or RNA to either: (1) increase the level of protein production; (2) decrease or stop the production of a protein; (3) inhibit the action of a protein; (4) inhibit proliferation or accumulation of specific cell types; and (5) induce proliferation or accumulation of specific cell types. As an example, if a protein is being produced which causes the accumulation of inflammatory cells within the joint, the expression of this protein can be inhibited, or the action of this protein can be interfered with, altered, or changed.

EXAMPLES

The examples below are non-limiting and are merely representative of various aspects and features of the present invention. The examples below demonstrate the isolation, and characterization of SRC-1 and provide evidence indicating that SRC-1 is a coactivator for steroid receptors.

EXPERIMENTAL PROCEDURES

All reagent for buffers and solutions were certified A.C.S. grade. When required, molecular grade reagents were used. All recombinant DNA works were performed according to standard procedures (Ausubel, F. M., et al., (1992), *Short Protocols In Molecular Biology*. New York: Greene Publishing Associates and John Wiley & Sons). Plasmid DNA constructs were prepared and purified using the plasmid DNA isolation kit (QIAGEN) and confirmed by sequence using deazadideoxy NTPs and Sequenase version 2.0 (U.S. biochemical).

Plasmid Construction.

The $GAL4_{DBD}$-$PR_{LBD}$ chimeric protien was constructed in the pAS1 yeast expression plasmid (Durfee, T. et al., (1993), *Genes and Dev.* 7, 555–569). The coding sequence from amino acid 631–933 of $hPR_B$ in the vector $YEphPR_B$ (Vegeto, E. et al., (1992), *Cell* 69, 703–713) was PCR amplified using Taq polymerase (Promega) with the primers CGCCATGGTCCTTGGAGGT (SEQ ID NO: 1) (upper strand) and AAGTCGACACATTCACTTTTTATGAAA-GAGAAG (SEQ ID NO: 2) (lower strand).

The primers were designed to contain NcoI and SalI restriction enzyme sites at 5' and 3' end of the amplified product. Amplification was carried out according to manufacturer conditions for 40 cycles (2 min 94° C., 2 min 45° C., 3 min 72° C.) with a final extension of 10 min at 72° C. The amplified product was then double-digested with NcoI and SalI, gel purified and inserted into the NcoI-SalI site of the vector pAS1 (Durfee, T. et al., (1993), *Genes and Dev.* 7, 555–569). For the two-hybrid screening, the NcoI-SalI insert was transferred into the pAS1-cyh vector which contains the cycloheximide marker for curing and selection in the Y190 yeast strain. The correct expression of the $GAL4_{DBD}$-$PR_{LB}D$ fusion protein in yeast was assessed by Dot and Western immunoblotting using the C262 monoclonal antibody and by hormone binding assays as previously described (Weigel, N. L. et al., (1992), *Mol. Endocrinol.* 6, 1585–1597).

For in vitro transcription and translation, SRC-1(0.8) cDNA XhoI fragment was cloned into the SalI site of the pT7BSalI vector (Baniahmad, A. et al., (1993), *Proc. Natl. Acad. Sce. USA* 90, 8832–8836). The SRC-1mut was constructed by cloning the SRC-1(0.8) BamHI-BglII fragment into the BglII-BamHI sites of the pABWgal mammalian expression vector (Baniahmad, A. et al., (1993), *Proc. Natl. Acad. Sci. USA* 90, 8832–8836).

The mammalian expression vectors and their reporter plasmids for $hPR_B$ (Vegeto, E. et al., (1992), *Cell* 69, 703–713) and PRE2-TATA-CAT (Beekman, J. M. et al., (1993), *Mol. Endocrinol.* 7, 1266–1274), hER (Smith, C. L. et al., (1993), *Proc. Natl. Acad. Sci. USA* 90, 6120–6124) and ERE2-TATA-CAT (Beekman, J. M. et al., (1993), *Mol. Endocrinol.* 7, 1266–1274), hGR (Giguere, V. et al., (1986), *Cell* 46, 645–652), hTR (Umesono, K. et al., (1991), *Cell* 65, 1255–12661), mouse RXR (Leng et al., 1994), DR4-tk-CAT and DR1-tk-CAT (Cooney, A. J. et al., (1993), *J. Biol Chem.* 268, 4152–4160), E2F and E2F-tk-CAT (Helin, K. et al., (1993), *Mol. Cell. Biol.* 13, 6501–6508), Sp1 and Sp1-tk-CAT (Courey, A. J. and Tjian, R. (1988), *Cell* 55, 887–898), CREB and CRE-tk-CAT (Chrivia, J. C. et al., (1993), *Nature* 365, 855) and GAL4VP16 and 17mer-tk-CAT (Baniahmad, A. et al., (1992), *EMBO J.* 11, 1015–1023) have been previously described and the above references are incorporated herein by reference in their entirety, including any drawings.

Two-hybrid Screening.

The yeast strain Y190 containing the GAL4$_{DBD}$-PR$_{LBD}$ expression plasmid was transformed with a human B-lymphocyte cDNA expression library constructed in the yeast expression vector pACT and the transformant screened for interacting proteins in the presence of $10^{-6}$ M progesterone as described by Durfee, T. et al., (1993), *Genes and Dev.* 7, 555–569. Library cDNA plasmids from positives clones were recovered and used to retransform Y190 cells containing the GAL4$_{DBD}$-PR$_{LB}$D or empty expression vectors as indicated herein.

The —galactosidase activities of the transformants in liquid culture were determined as described (Ausubel, F. M., et al., (1992), *Short Protocols In Molecular Biology*, New York: Greene Publishing Associates and John Wiley & Sons) using O-Nitrophenyl —D-galactopyranoside (ONPG) as a substrate. The specificity of the interacting proteins was assessed by mating Y190 cells containing the SRC-1(0.8) cDNA with the Y187 strain containing pAS1-SNF, pAS1-p53, pAS1-CDK or pAS1-lamin and the —galactosidase activity of the diploids were determined by filter lift or in liquid culture assays (Ausubel, F. M., et al., (1992), *Short Protocols In Molecular Biology*, New York: Greene Publishing Associates and John Wiley & Sons; Durfee, T. et al., (1993), *Genes and Dev.* 7, 555–569). In vitro protein-protein interactions.

Receptor-specific affinity resins were constructed by linking recombinant baculovirus glutathione-S-transferase hPR$_A$ (GST-hPR$_A$) to GST-Sepharose beads as previously described (Baniahmad, A. et al., (1995), *Mol. Cell Biol.* 15, 76–86). The GST-PR$_A$ fusion protein was constructed by inserting the PR$_A$ cDNA into baculovirus expression vector according to standard procedures (Beekman, J. M. et al., (1994), *Gene* 146, 285–289). Receptors were activated in vivo by the addition of $10^{-6}$ M hormones (progesterone or RU486) to intact cells for 24 h before harvesting. Receptors were then prepared as whole-cell extracts and treated for an additional 15 min at 30° C. with $10^{-6}$ M hormone before purification. Approximately 400 μg of total proteins were incubated with 20 μl of GST-Sepharose beads in suspension (Pharmacia) for 2 h at 4° C. Resins were then washed twice with NENT buffer (20 mM Tris-OH pH 8.0 containing 10 mM NaCl, 1 mM EDTA, 0.5% NP40 and 0.5% milk powder) and twice more with transcription buffer (20 mM HEPES pH 7.9 containing 60 mM NaCl, 1mM dithiothreitol, 6 mM MgCl2, 0.1 mM EDTA and 10% Glycerol).

Subsequently, beads containing purified receptors were mixed with 25 μl of crude lysate of in vitro transcribed and translated [$^{35}$S]met-SRC-1(0.8) (Promega) and interactions were allowed to occur at 4° C. for 1 h in an end-over-end rotator in 200 μl of transcription buffer. After interactions, beads were washed once with NENT buffer, three times with NENT buffer without milk powder and twice with transcription buffer. Bound proteins were then eluted with 0.2% sodium dodecyl sulfate (SDS) in 10 mM Tris-OH buffer (pH7.6), fractionated on SDS-PAGE and subjected to fluorography for $^{35}$S as described (Baniahmad, C. et al., (1995), *Mol. Endocrinol.* 9, 34–43). The input lane represents 10% of the total volume of the crude lysate used in each reaction. The amount of receptor in the beads was estimated by commassie blue-staining of the GST-hPR$_A$ eluted from the affinity resins and fractionated on SDS-PAGE.

RNA Analysis.

Northern blot membranes containing poly(A)$^+$ RNAs from different human organs (Clontech) or isolated from different cell lines (Invitrogen) were hybridized at 42° C. in 50 formamide with 5×10$^5$ cpm/ml of the [$^{32}$P] random primed labeled SRC-1(0.8) XhoI insert for 36 h as described (Ausubel, F. M., et al., (1992), *Short Protocols In Molecular Biology*, New York: Greene Publishing Associates and John Wiley and Sons). After hybridization, a final wash in 0.25× SSC, 0.1% SDS at 65° C. was performed and then membranes submitted to autoradiography using Kodak X-OMAT Imaging films.

Following the identification of SRC-1(0.8), the XhoI insert cDNA was used to screen a fibroblast library constructed in λZAP (Pereira, F. et al., (1992), *Biochem. Biophys. Res. Commun.* 175, 831–838) according to standard procedures (Ausubel, F. M., et al., (1992), *Short Protocols In Molecular Biology*, New York: Greene Publishing Associates and John Wiley & Sons). Several clones were identified and isolated. Sequence comparison revealed that two of them, 154–22a of 1.4 kb and 154–25 of 2.3 kb, encompass 3.6 kb of the most 3' end of SRC-1. The clone 154–22a also contained additional 0.8 kb of 5' sequence not related to SRC-1, which were excised by subcloning the XhoI (filled) insert into the PvuII site of pABWgal vector. The remaining 5' end sequence of SRC-1 was cloned by PCR amplification from a λgt11 HeLa library (Clontech) using 10$^9$ phages with the λgt11 forward primer and the nested primer GGAAT-TCCCGACGTTGTGCCAACA (SEQ ID NO: 3).

Amplification was carried out using Taq polymerase under manufacturer conditions in two steps. First, amplification was performed for 1 min 94° C., 1 min 72° C., 2 min 72° C. followed for another five cycles with a progressive decrease in the annealing temperature of one degree Celsius per cycle, from 71° C. to 67° C. Then, amplification continued for 29 cycles (1 min 94° C., 1 min 64° C., 2 min 72° C.) with a final extension of 5 min 72° C. The PCR products were cloned into the pCRII TA-cloning vector (Invitrogen) using either the direct PCR product or the >1.6 kb sized product purified on a 1% agarose gel. Clones ranging from 0.6 to 2.2 kb were subjected to sequence using the nested oligo as primer. Amplified cDNAs containing identical sequence to the 5' end of 154–22a were assigned as positives. The EcoRI (partial) and BsmI insert from the longest cDNA amplified (2.2 kb) was ligated to the BsmI-SalI insert from 154–22a and then religated into the EcoRI-XhoI sites of the mammalian expression vector pBK-CMV (Strategene) and renamed SRC-1. The sequence of the PCR amplified open reading frame of SRC-1 represents the data originated from two independent PCR-amplified products. The 3' end untranslated region of SRC-1 from clone 154–25 (2.3 kb) was not included.

Transient Transfection and CAT Assays.

Cells were maintained in Dulbecco's modified Eagle's medium supplemented with 10% (vol/vol) fetal calf serum (Smith, C. L. et al., (1993), *Proc. Natl. Acad. Sci. USA* 90, 6120–6124). The day before transfection, $10^6$ cells were seeded in 100 mm dishes and 4–6 h later switched serum-free medium supplemented with Nutridoma-SR (Boehringer Mannhein). When ER was used for transfections, phenol-red-free medium was used (Smith, C. L. et al., (1993), *Proc. Natl. Acad. Sci. USA* 90, 6120–6124). HeLa cells were transfected with mammalian expression vectors encoding steroid receptors or other transcription factors along with 5 μg of CAT reporter. Lipofectin (GibcoBRL) was selected for transfection of Hela cells. CVI and Lmtk⁻ cells were transfected using polybrene (Sigma) as previously described (Denner, L. A. et al., (1990), *Science* 250, 1740–1743).

After transfection, excess DNA was removed and cells were treated for 42 h with media containing hormones as indicated in figure legends. Cells were then harvested and proteins prepared as whole-cell extracts by freeze-thaw lysis. The reporter CAT activity in the extract was determined using 100 uCi of $[^{14}C]$-chloramphenicol and 4 mM acetyl coenzyme A as substrate and standardized by protein content. Activity of the extract was calculated by determining the percentage of conversion of $[^{14}C]$-chloramphenicol to the mono and diacetylated forms (Ausubel, F. M., et al., (1992), *Short Protocols In Molecular Biology*, New York: Greene Publishing Associates and John Wiley & Sons).

Example 1
Isolation and Characterization of PR Interacting Proteins.

Human PR contains a ligand-inducible transactivation function in the C-terminus of its ligand-binding domain (Meyer, M. E. et al., (1990), *EMBO J.* 9, 3923–3932; Gronemeyer, H. (1991), *Ann. Rev. Genet.* 25, 89–123). To isolate cDNAs encoding proteins that specifically interact with the hormone binding domain of PR, we used the yeast two-hybrid system previously described by Durfee, T. et al., (1993), *Genes and Dev.* 7, 555–569, incorporated herein by reference in its entirety, including any drawings. First we constructed a chimeric protein between the yeast transcription factor $GAL4_{DBD}$ (amino acid 1–147) and the region of hPR that encompasses the hinge and the LBD ($PR_{LBD}$, amino acid 362–933) in the vector pAS1. Yeast Y190 cells expressing $GAL4_{DBD}$-$PR_{LB}$D fusion protein were then transformed with a B lymphocyte cDNA library fused to the yeast GAL4 activation domain ($GAL4_{AD}$).

The yeast strain Y190 provides a dual reporter system to screen for cDNAs encoding proteins that interact with $PR_{LBD}$: HIS3 for histidine prototrophy and LacZ for —galactosidase activity, both of which are chromosomally integrated and their expression regulated by a GAL4 promoter. Interaction between $GAL4_{DBD}$-$PR_{LB}$D and the cDNA encoded protein fused to the $GAL4_{AD}$ (amino acid 768 to 880) will result in the activation of the chromosomal integrated HIS3 and LacZ gene transcription under the control of the galactose-inducible UASG promoter. Cells grown in selective media for histidine prototrophy and for their blue phenotype in the presence of X-gal and $10^{-6}$ M progesterone. From approximately 600,000 yeast colonies that were screened in the presence of $10^{-6}$ M progesterone, seven positive clones were obtained. Their interaction with the $PR_{LBD}$ was specific since they failed to interact with other unrelated proteins such as p53, lamin, CDK and SNF1, when fused to the $GAL4_{DBD}$.

From those seven isolated cDNAs, the one [SRC-1(0.8)] that exhibited the strongest interaction with the $PR_{LBD}$ in the presence of $10^{-6}$ M progesterone, was selected for further studies. Galactosidase activity was only observed when the $PR_{LBD}$ was coexpressed with SRC-1(0.8) cDNA fused to the GAL4 activation domain. Neither SRC-1(0.8) nor $PR_{LB}$D fusion proteins were active when expressed alone. SNF1 and SNF4, two proteins previously described to interact in the two-hybrid system were used as a positive control (Durfee et al., (1993), *Genes and Dev.* 7:555–569). In order to eliminate the possibility that failure of the $GAL4_{DBD}$-$PR_{LBD}$ construct to activate the LacZ reporter is due to lack of expression, the $GAL4_{DBD}$-$PR_{LBD}$ fusion protein level was determined. Dot- and Western immunoblotting which were carried out with the C262 anti-hPR monoclonal antibody that recognizes the last 14 amino acid in the C-terminus of hPR (Weigel, N. L. et al., (1992), *Mol. Endocrinol.* 6, 1585–1597) indicates that the $GAL4_{DBD}$-$PR_{LB}$D fusion protein was expressed correctly in yeast cells. In addition, ligand-binding assays revealed that the $GAL4_{DBD}$-$PR_{LB}$D fusion protein was expressed in yeast at 0.93±0.12 (Xn=7±SE) pmol/mg of protein.

Example 2
SRC-1 Interacts with Receptor in a Ligand-dependent Manner.

We examined whether the interaction of SRC-1(0.8) with PR was hormone dependent. First, we carried out interactions in the yeast two-hybrid system. Yeast cells expressing $GAL4_{DBD}$-$PR_{LB}$D and SRC-1(0.8) were grown in selective media containing $10^{-6}$ M progesterone, no hormone or $10^{-6}$ M RU486 and the —galactosidase activity determined as in Example 1. The interaction was significantly reduced when the receptor was either free of ligand or bound to RU486. Both progesterone and RU486 had no effect on the activity of $PR_{LBD}$ or SRC-1(0.8) alone; no major effect of the ligands on the SNF1/SNF4 positive control was observed. To substantiate further that the ligand-dependent interaction observed in intact cells is due to a direct interaction with the receptor protein, we also performed an in vitro binding assay using $PR_A$. The $hPR_A$ cDNA was fused to glutathione-S-transferase (GST) sequence in a baculovirus expression vector to generate GST-$PR_A$ fusion protein suitable for expression in Sf9 insect cells as described herein, i.e. radiolabeled $[^{35}S]$ met SRC-1(0.8) was incubated in batch with purified baculovirus expressed GST-$PR_A$ fusion protein bound to glutathione-Sepharose beads either in the absence or in the presence of $10^{-6}$ M progesterone or RU486. GST-$PR_A$ was linked to glutathione sepharose beads and used as an affinity matrix for binding studies. Bound radiolabeled [35S] met SRC-1(0.8) was then eluted and analyzed in a 15% SDS-PAGE and subjected to fluorography as described herein. SDS-PAGE analysis of the GST-$PR_A$ eluted from the glutathione affinity column indicated that it is indeed expressed in a full-length form.

In vitro transcribed and translated $[^{35}S]$SRC-1(0.8) was retained by the GST-$PR_A$ affinity columns when the receptor was bound to progesterone. Significantly lesser interactions were observed with ligand-free or RU486 bound receptor. Little or no binding was observed on the GST protein column without $PR_A$.

Thus, interaction of SRC-1(0.8) with PR occurred in vivo and in vitro in a ligand-dependent manner and this interaction involved the ligand binding domain. Our conclusion was substantiated further by an observation that the N-terminal region of $PR_A$ (amino acids 165–565) fused to the GAL4DBD failed to interact with SRC-1(0.8) in the two-hybrid system.

Example 3
Isolation of Full-length SRC-1.

To obtain a full-length cDNA, conventional screening of a fibroblast library with SRC-1(0.8 kb) cDNA as probe was carried out. We isolated two clones of 1.4 kb and 2.3 kb that encompass most of the 3' end of SRC-1. The 5' end of SRC-1 (2.2 kb), was cloned by PCR from a HeLa cell library using nested primers as described herein. Sequence alignment of these three isolated clones revealed a 5.6 kb cDNA containing an open reading frame of 1061 amino acids with a predicted mass of 114.1 kDa and apparent molecular size of ~125 kDa on SDS-PAGE after in vitro transcription and translation.

Current sequence comparisons using the BLAST algorithm show that amino acids 605 to 1005 are identical to the hin-2 gene. This gene was identified by analysis of a human immunodeficiency virus type 1 promoter insertion in vivo (access number U19179). Sequence comparison reveals that the hin-2 gene contains a 54 bp insertion. This DNA insertion introduces a stop codon after 14 amino acids downstream, resulting in a premature termination of SRC-1. In addition, partial DNA sequences for SRC-1 have been isolated randomly (access numbers T56159 and U19179). No function for these partial cDNAs has been described. SRC-1 sequence comparisons at the amino acid level show no significant homology to any known protein. A notable glutamine rich region (31.4% Q) is observed between residues 673 and 758. The N-terminus of SRC-1 (residues 258–350) is serine and threonine rich (22.6% S and 11.8% T). In addition, there are regions noted for their leucine and proline content (9.2% L and 9.6% P).

Example 4
Expression of SRC-1 mRNAs.

Northern blot analysis using poly $A^+$ RNA from human tissue and cell lines was carried out to determine the size and distribution of SRC-1 mRNA. Hybridization was performed with the [$^{32}$P] radiolabeled SRC-1(0.8) cDNA. Analysis of actin mRNA was performed to control for loading and integrity of the RNAs. SRC-1 is expressed as two mRNAs of approximately 5.5 and 7.5 kb in a variety of tissues, including heart, placenta, lung, liver, smooth muscle, kidney and pancreas. In brain, SRC-1 was predominantly expressed as a 7.5 kb mRNA. All other human tissues analyzed (spleen, thymus, prostate, testis, ovary, small intestine, colon and leukocytes), as well as cell lines (HeLa, CV-1 and Jurkat) exhibited the same two SRC-1 mRNAs, but with some variation in expression level.

Example 5
Transient Expression of SRC-1 Stimulates Ligand-bound hPR Transactivation.

To further investigate the role of SRC-1 in receptor transactivation of target gene expression, transient transfection assays were carried out in mammalian cell lines. HeLa cells were cotransfected with mammalian expression vectors for full-length SRC-1 and hPR$_B$ together with a plasmid containing two copies of the progesterone-responsive DNA element (PRE) inserted in front of the TATA box of the E1b adenovirus, linked to the chloramphenicol acetyl transferase (CAT) reporter gene, PRE2-TATA-CAT.

In particular, HeLa cells were transiently transfected with 5 $\mu$g of PRE2-TATA-CAT or ERE2-TATA-CAT reporter plasmids along with 0.5 $\mu$g of hPR$_B$ mammalian expression plasmid and 3 $\mu$g of SRC-1 or empty expression vector, either in the absence or in the presence of $2 \times 10^{-8}$ M progesterone agonist R5020. Cells were harvested 42 h after transfection and the chloramphenicol acetyl transferase (CAT) activity determined using 8 $\mu$g of protein extract.

Ligand-free hPR has minimal activity on the reporter either in the absence or in the presence of SRC-1. Addition of the progesterone agonist R5020 resulted in a ~5 fold induction of hPR activity. However, when SRC-1 full-length cDNA was coexpressed with hPR in the presence of hormone, a 14.0±3.3 (Xn=7±SEM) fold induction over the hormone-induced receptor activity was observed (an average of seven experiments).

To further confirm that the stimulation observed by coexpression of SRC-1 with hPR was solely dependent on hPR, and not to an indirect effect on the basal activity of the reporter, we replaced the PRE reporter construct with an ERE reporter, ERE2-TATA-CAT.

In particular, HeLa cells were transfected with PRE2-TATA-CAT and hPR$_B$ along with SRC-1 or empty expression vector in the absence or in the presence of $2 \times 10^{-8}$ M R5020 alone or in combination with $4 \times 10^{-8}$ M RU486 and then assayed for CAT activity using 14 $\mu$g of proteins extract.

In the absence of PR binding site there is no effect of SRC-1 on the reporter construct activity, either in the absence or in the presence of the ligand. These results indicate that SRC-1 enhancement of hPR transactivation occurs via ligand-bound receptor; it does not independently affect the basal transcription machinery. We investigated the effect of SRC-1 on transactivation of hPR bound to the antagonist RU486. Again, SRC-1 enhanced hPR activity in the presence of the agonist R5020. Addition of RU486 to intact cells prevented the hormone-induced transactivation of hPR. Coexpression of SRC-1 with the antagonist-bound receptor was unable to augment and/or recover to any extent the RU486-antagonized receptor transcriptional activity of the reporter gene.

Taken together, these findings indicate that SRC-1 acts directly on the agonist-bound receptor protein to modulate its transcriptional activity without a major effect on the basal promoter and fulfills the general definition of a coactivator. In addition, evidence is provided that a steroid receptor coactivator can discriminate between an agonist and an antagonist receptor complex bound to DNA in vivo.

Example 6
SRC-1 Acts as a Coactivator for hPR by Reversing Receptor Squelching.

To substantiate the coactivator function of SRC-1 we utilized a more stringent assay for coactivators that has been proposed to exploit the property of excess activator to sequester a limited pool of nuclear coactivator (Flanagan, P. M. et al., (1991), *Nature* 350, 436–438). It has been reported earlier that overexpression of ER can squelch PR-dependent transcriptional activity in cells (Meyer, M. E. et al., (1989), *Cell* 57, 433–442; Conneely, O. M. et al., (1989), "Promoter specific activating domains of the chicken progesterone receptor." In Gene Regulation by Steroid Hormones IV. A. K. Roy and J. Clark, eds. (New York, Berlin, Heidelberg, London, Paris, Tokyo: Springer-Verlag), pp. 220–223). This finding suggests the existence of a common limiting factor (s) necessary for these two receptors to transactivate target genes. We asked whether the coexpression of SRC-1 was able to reverse this squelching.

HeLa cells were transfected with 1 $\mu$g of both hPR and hER expression vectors, together with 5 $\mu$g of PRE2-TATA-CAT and increasing amounts of SRC-1. Cells were then exposed to ligands R5020 and/or E2 ($2 \times 10^{-8}$ M) and CAT activities determined 42 h later using 40 $\mu$g of proteins extract. The percentage of chloramphenicol conversion to the mono and diacetylated form was determined and represents the average of three independent experiments (Xn= 3±SEM).

The hormone-induced transcriptional activity mediated by hPR is inhibited ~19 fold upon coexpression of ligand-bound hER. Addition of SRC-1 reversed this squelching by ~16 fold in a dose-dependent manner. Could this increase be explained by the enhancement of residual PR that remains unsquelched during the assay? We think not since a ~5 fold stimulation of PR transactivation is observed at the highest concentration of SRC-1 (2 μg), as compared to a 16 fold recovery in the presence of estrogen. Such quantitative differences in activation argue strongly for reversal of squelching. We conclude that SRC-1 is a limiting factor necessary for efficient PR and ER transactivation.

Example 7

SRC-1 is a Coactivator for Multiple Steroid Receptor Superfamily Members.

The ability of SRC-1 to reverse squelching between two different members of the steroid receptor superfamily suggested that SRC-1 might be a general coactivator for members of the steroid receptor superfamily. In fact, the N-terminally truncated form of SRC-1, SRC-1(0.8) also was able to interact with baculovirus expressed GST-ER and GST-TR in vitro. Thus, we investigated the effect of SRC-1 expression on the transcriptional activity of other intracellular receptors.

HeLa cells were cotransfected with 0.5 μg of cDNAs encoding various steroid receptors indicated and 5 μg of their cognates HREs containing reporters, including PR/PRE2-TATA-CAT, ER/ERE2-TATA-CAT, GR/PRE2-TATA-CAT, TR-/DR4-tk-CAT and RXR/DR1-tk-CAT, along with 3 μg of SRC-1 or empty expression vector. Cells were then treated with their corresponding ligands (PR:R5020, ER:estradiol, GR:dexamethasone, TR:Triac, RXR:9-cis retinoic acid) at a concentration of $2 \times 10^{-8}$ M. The CAT activity of the reporter was determined using 14 μg of protein extract.

SRC-1 can enhance PR, as well as ER, GR, TR and RXR transcriptional activity through their cognate DNA response-elements. Therefore, SRC-1 appears to be a general coactivator for all members of the nuclear receptors superfamily tested to date.

HeLa cells were transfected as described above with various activators and their cognates DNA-elements containing reporter, including the chimera GAL4-VP16/$UAS_G$-tk-CAT, Sp1/Sp1-tk-CAT, E2F/E2F-tk-CAT, and CREB/CRE-tk-CAT in the absence and in the presence of 1 μM forskolin (Fsk) along with SRC-1 or empty expression vector. The CAT activity of the reporter was determined. Each assay is representative of at least two independent experiments.

To determine the spectrum of action of SRC-1 we examined its effect on selected transactivators. We observed that SRC-1 enhanced the transcriptional activity of GAL4-VP16 chimera protein through the $UAS_G$ element. Albeit to a lesser extent, SRC-1 can also enhance Sp1 transcriptional activity. In contrast, SRC-1 did not alter the transcriptional activity of other nuclear factors such as E2F and E47. We tested whether SRC-1 could influence the transcriptional activity of an unrelated inducible transcriptional factor such as CREB (Chrivia, J. C. et al., (1993), *Nature* 365, 855).

CREB activity can be induced by the addition of forskolin to intact cells. Coexpression of SRC-1 did not affect either basal nor forskolin-stimulated transcriptional activities of CREB. Therefore, while SRC-1 enhances the activity of members of the steroid/thyroid superfamily of receptors, it is not a general coactivator for all classes of transactivators.

Example 8

The Truncated C-terminal Region of SRC-1 Acts as a Dominant Negative Regulator of Steroid Receptor Function.

To further elucidate the mechanism of SRC-1 action, the effect of the N-terminal deletion mutant of SRC-1, SRC-1 (0.8), on receptor transactivation was examined. The amino acid sequence from 865–1061, which contains the region that binds to the receptor, was cloned in frame to a mammalian expression vector that provided an exogenous AUG codon.

Lmtk⁻ cells were transfected with 5 μg of steroid receptors cDNAs expression vectors and their reporters, PR/PRE2-tk-CAT and TR§/DR4-tk-CAT, along with 10 μg of SRC-1(0.8) or empty expression vector and then treated with hormones ($2 \times 10^{-8}$ M). The reporter CAT activity was determined using 60 μg of protein extract.

The hormone induced transcriptional activity of hPR can be efficiently reduced by the coexpression of SRC-1(0.8) in Lmtk⁻ cells. SRC-1(0.8) also inhibits the ligand-induced transcriptional activity of TR. No major effect on the hormone-free receptor was observed. SRC-1(0.8) also interfered with hPR transcriptional activity in HeLa and CV1 cells to a similar extent. The capability of the truncated SRC-1(0.8) to act as dominant-negative repressor on steroid induced receptor transcriptional activity further suggests that SRC-1 is a genuine coactivator for steroid receptor target gene expression. Also these results provide preliminary insight into the functional regions of SRC-1 with respect to transcriptional activation.

Although certain embodiments and examples have been used to describe the present invention, it will be apparent to those skilled in the art that changes to the embodiments and examples shown may be made without departing from the scope or spirit of the invention.

Those references not previously incorporated herein by reference, including both patent and non-patent references, are expressly incorporated herein by reference for all purposes.

Other embodiments are within the following claims.

What is claimed is:

1. An isolated nucleic acid comprising a nucleic acid sequence encoding SEQ ID NO: 5.

2. The isolated nucleic acid in claim 1 wherein the nucleic acid sequence is SEQ ID NO: 4.

3. An isolated nucleic acid comprising a nucleic acid sequence encoding amino acids 865 to 1061 of SEQ ID NO: 5.

4. The isolated nucleic acid in claim 3 wherein the nucleic acid sequence is 2594 to 3183 of SEQ ID NO: 4.

* * * * *